US010758137B2

(12) United States Patent
Deno et al.

(10) Patent No.: US 10,758,137 B2
(45) Date of Patent: Sep. 1, 2020

(54) ORIENTATION INDEPENDENT SENSING, MAPPING, INTERFACE AND ANALYSIS SYSTEMS AND METHODS

(71) Applicant: St. Jude Medical, Cardiology Division, Inc., St. Paul, MN (US)

(72) Inventors: Don Curtis Deno, Andover, MN (US); Dennis J. Morgan, N. Crystal, MN (US); Joshua C. Bush, Minneapolis, MN (US); Kumaraswamy Nanthakumar, Mississauga (CA); Stephane Masse, Toronto (CA); Karl Magtibay, Milton (CA)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 21 days.

(21) Appl. No.: 15/953,155

(22) Filed: Apr. 13, 2018

(65) Prior Publication Data
US 2018/0296111 A1    Oct. 18, 2018

Related U.S. Application Data

(60) Provisional application No. 62/485,875, filed on Apr. 14, 2017.

(51) Int. Cl.
*A61B 34/20* (2016.01)
*A61B 18/14* (2006.01)
(Continued)

(52) U.S. Cl.
CPC .......... *A61B 5/04011* (2013.01); *A61B 5/044* (2013.01); *A61B 5/046* (2013.01);
(Continued)

(58) Field of Classification Search
CPC .......... A61B 34/20; A61B 18/14; A61B 5/04; A61B 5/042; A61B 5/7221; A61B 5/0422;
(Continued)

(56) References Cited

U.S. PATENT DOCUMENTS 4,649,924 A    3/1987 Taccardi
5,297,549 A    3/1994 Beatty et al.
(Continued)

FOREIGN PATENT DOCUMENTS

EP    1166714    1/2002
EP    1336379    8/2003
(Continued)

OTHER PUBLICATIONS

Mazeh et al., "A Simplified Approach for Simultaneous Measurements of Wavefront Velocity and Curvature in the Heart Using Activation Times", Cardiovascular Engineering and Technology, 4:4 (Dec. 2013) pp. 520-534.
(Continued)

*Primary Examiner* — Jon Eric C Morales
(74) *Attorney, Agent, or Firm* — Wiley Rein LLP

(57) ABSTRACT

The disclosure relates generally to applications of Orientation Independent Sensing (OIS) and Omnipolar mapping Technology (OT) to various system, device and method embodiments as recited herein. Similarly, systems and methods suitable for supporting OIS and OT systems and methods are disclosed. Further, OIS and OT implementations that provide end user interfaces, diagnostic indicia and visual displays generated, in part, based on measured data or derived from measured data are also disclosed. Embodiments also describe applying optimization techniques to determine the greatest voltage difference of a local electric field associated with an electrode-based diagnostic proce-
(Continued)

dure and a vector representation thereof. Various graphic user interface related features are also described to facilitate orientation and electrode clique signal display.

24 Claims, 24 Drawing Sheets
(16 of 24 Drawing Sheet(s) Filed in Color)

(51) Int. Cl.
*A61B 5/04* (2006.01)
*G06F 3/0482* (2013.01)
*A61B 5/042* (2006.01)
*A61B 5/00* (2006.01)
*A61B 5/044* (2006.01)
*A61B 5/046* (2006.01)
*A61B 5/0432* (2006.01)

(52) U.S. Cl.
CPC ........ *A61B 5/04017* (2013.01); *A61B 5/0422* (2013.01); *A61B 5/0432* (2013.01); *A61B 5/7203* (2013.01); *A61B 5/746* (2013.01); *G06F 3/0482* (2013.01)

(58) Field of Classification Search
CPC ............ A61B 18/1492; A61B 5/04017; A61B 5/6858; A61B 2018/00577; A61B 2034/2053; A61B 2090/064; A61B 2017/00053; A61B 2018/00267; A61B 2018/00648; A61B 5/00; A61B 5/0432; A61B 5/044; A61B 5/046; A61B 5/04011; A61B 5/7203; A61B 5/746; G06F 3/0482
See application file for complete search history.

(56) References Cited

U.S. PATENT DOCUMENTS

| | | |
|---|---|---|
| 5,546,270 A | 8/1996 | Konno et al. |
| 5,848,972 A | 12/1998 | Triedman et al. |
| 5,921,923 A | 7/1999 | Kuck et al. |
| 6,233,476 B1 | 5/2001 | Strommer et al. |
| 6,360,121 B1 | 3/2002 | Shoda et al. |
| 6,400,981 B1 | 6/2002 | Govari |
| 6,498,944 B1 | 12/2002 | Ben-Haim et al. |
| 6,690,963 B2 | 2/2004 | Ben-Haim et al. |
| 6,788,967 B2 | 9/2004 | Ben-Haim et al. |
| 7,197,354 B2 | 3/2007 | Sobe |
| 7,263,397 B2 | 8/2007 | Hauck et al. |
| 7,386,339 B2 | 6/2008 | Strommer et al. |
| 8,862,213 B2 | 10/2014 | Lo et al. |
| 8,876,817 B2 | 11/2014 | Avitall et al. |
| 2006/0253030 A1 | 11/2006 | Altmann et al. |
| 2007/0225589 A1 | 9/2007 | Viswanathan |
| 2008/0183088 A1 | 7/2008 | Lian et al. |
| 2008/0221643 A1 | 9/2008 | Olson |
| 2009/0248014 A1 | 10/2009 | Shachar et al. |
| 2010/0168557 A1 | 7/2010 | Deno et al. |
| 2010/0168560 A1 | 7/2010 | Hauck et al. |
| 2013/0190747 A1 | 7/2013 | Avitall et al. |
| 2013/0274582 A1 | 10/2013 | Afonso et al. |
| 2014/0058375 A1 | 2/2014 | Koblish |
| 2014/0235996 A1 | 8/2014 | Kim et al. |
| 2014/0336518 A1 | 11/2014 | Shuros et al. |
| 2014/0343442 A1 | 11/2014 | Thakur et al. |
| 2016/0045133 A1 | 2/2016 | Balachandran et al. |
| 2016/0331471 A1* | 11/2016 | Deno .................... A61B 34/20 |
| 2017/0042449 A1 | 2/2017 | Deno et al. |
| 2017/0049348 A1 | 2/2017 | Deno et al. |

FOREIGN PATENT DOCUMENTS

| | | |
|---|---|---|
| EP | 2186474 | 5/2010 |
| JP | 11047148 | 2/1999 |
| JP | 2001-061789 | 3/2001 |
| JP | 2002-051998 | 2/2002 |
| JP | 2007537831 | 12/2007 |
| JP | 2012524606 | 10/2012 |
| WO | 1997/024983 | 7/1997 |
| WO | 2012/037471 | 3/2012 |
| WO | 2012-092016 | 7/2012 |
| WO | 2014/113612 | 7/2014 |
| WO | 2014/182822 | 11/2014 |
| WO | 2015/130824 | 9/2015 |
| WO | 2016/183247 | 11/2016 |

OTHER PUBLICATIONS

Michaud et al., "Information at our Catheter Tips: Unipolar Electrogram Morphology Makes another Comeback!", Heart Rhythm, 7:9 (Sep. 2010) pp. 1301-1302.
Mironov et al., "Role of Conduction Velocity Restitution and Short-Term Memory in the Development of Action Potential Duration Altemans in Isolated Rabbit Hearts", Circulation (Jul. 1, 2008), pp. 17-25.
Mountantonakis et al., "Relationship between Voltage Map "Channels" and the Location of Critical Isthmus Sites in Patients with Post-Infarction Cardiomyopathy and Ventricular Tachycardia", JACC 61:20 (May 21, 2013), pp. 2088-2095.
Nanthakumar et al., "Regional Differences in Ventricular Fibrillation in the Open-Chest Porcine Left Ventricle"Circulation Research (Oct. 18, 2002), pp. 733-740.
Narayan et al., "Treatment of Atrial Fibrillation by the Ablation of Localized Sources", JACC 60:7 (Aug. 14, 2012) pp. 628-636.
Nayyar et al., "High-Density Mapping of Ventricular Scar a Comparison of Ventricular Tachycardia (VT) Supporting Channels with Channels that do not Support VT", Circulation (Feb. 2014), pp. 90-98.
Otomo et al., "Local Unipolar and Bipolar Electrogram Criteria for Evaluating the Transmurality of Atrial Oblation Lesions at Different Catheter Orientations Relative to the Endocardial Surface", Heart Rhythm 7:9 (Sep. 2010), pp. 1291-1300.
Parson et al.,"Cardiac Mapping Instrumentation for the Instantaneous Display of Endocardial and Epicardial Activation", IEEE Transactions on Biomedical Engineering, vol. BME-34, No. 6 (Jun. 1987), pp. 468-472.
Patel et al., "Electroanatomic Mapping of the Intercaval Bundle in Atrial Fibrillation", Circulation (Dec. 2014) pp. 1262-1267.
Pieper et al., "Simultaneously Collected Monopolar and Discrete Bipolar Electrograms: Comparison of Activation Time Detection Algorithms", PACE, vol. 16 (Mar. 1993), pp. 426-433.
Plank et al., "Cardiac Near-Field Morphology During Conduction Around a Microscopic Obstacle-a Computer Simulation Study", Annals of Biomedical Engineering, 31:10 (Nov. 2003), pp. 1206-1212.
Plank et al., "Model Study of Vector-Loop Morphology During Electrical Mapping of Microscopic Conduction in Cardiac Tissue", Annals of Biomedical Engineering, 28:10 (Oct. 2000), pp. 1244-1252.
Plank et al., "Use of Cardiac Electric Near-Field Measurements to Determine Activation Times", Annals of Biomedical Engineering, 31:9 (Oct. 2003) pp. 1066-1076.
Price et al., "Novel Ablation Catheter Technology that Improves Mapping Resolution and Monitoring of Lesion Maturation", The Journal of Innovations in Cardiac Rhythm Management, (Jan. 2012), pp. 599-609.
Ravelli et al., "Wave Similarity Mapping Shows the Spatiotemporal Distribution of Fibrillatory Wave Complexity in the Human Right Atrium During Paroxysmal and Chronic Atrial Fibrillation", Journal of Cardiovascular Electrophysiology, 16:10 (Oct. 2005), pp. 1071-1076.

(56) References Cited

OTHER PUBLICATIONS

Rogers et al., "Quantitative Techniques for Analyzing High-Resolution Cardiac-Mapping Data", IEEE Engineering in Medicine and Biology, 17:1 (Jan./Feb. 1998), pp. 62-72.
Schilling et al., "Simultaneous Endocardial Mapping in the Human Left Ventricle Using a Noncontact Catheter Comparison of Contact and Reconstructed Electrograms During Sinus Rhythm", Circulation (Sep. 1, 1998), pp. 887-898.
Schmitt et al., "Symposium on Electrocardiography and Vectorcardiography the Present Status of Vectorcardiography", JAMA Internal Medicine 96:5 (Nov. 1955), pp. 574-590.
Schuler et al., "Influence of Catheter Orientation, Tissue Thickness and Conduction Velocity on the Intracardiac Electrogram", Biomed Tech 2013; 58 (Suppl. 1) 2 pages.
Schumacher et al., "Transverse Conduction Capabilities of the Crista Terminalis in Patients with Atrial Flutter and Atrial Fibrillation", JACC 34:2 (Aug. 1999) pp. 363-373.
Shors et al., "A method for Determining High-Resolution Activation Time Delays in Unipolar Cardiac Mapping"; IEEE Transactions on Biomedical Engineering, 43:12 (Dec. 1996) pp. 1192-1196.
Spears et al., "Relationship of Bipolar and Unipolar Electrogram Voltage to Scar Transmurality and Composition Derived by Magnetic Resonance Imaging in Patients with Nonischemic Cardiomyopathy Undergoing VT Ablation", Heart Rhythm 9:11 (Nov. 2012) pp. 1837-1846.
Stevenson et al., "Recording Techniques for Clinical Electrophysiology", Journal of Cardiovascular Electrophysiology 16:9 (Sep. 2005) pp. 1017-1022.
Tedrow et al., "Recording and Interpreting Unipolar Electrograms to Guide Catheter Ablation", Heart Rhythm 8:5 (May 2011) pp. 791-796.
Thompson et al., "Improved Spatial Resolution and Electrogram Wave Direction Independence with the Use of an Orthogonal Electrode Configuration", J Clin Monit Comput 28: (Apr. 2014), pp. 157-163.
Tungjitkusolmun et al., "Guidelines for Predicting Lesion Size at Common Endocardial Locations During Radio-Frequency Ablation", IEEE Transactions on Biomedical Engineering 48:2 (Feb. 2001) pp. 194-201.
Weber et al., "Conduction Velocity Restitution of the Human Atrium-An Efficient Measurement Protocol for Clinical Electrophysiological Studies"; IEEE Transactions on Biomedical Engineering, 58:9 (Sep. 2011) pp. 2648-2655.
Weber et al., "Wave-Direction and Conduction-Velocity Analysis from Intracardiac Electrograms—A Single-Shot Technique", IEEE Transactions on Biomedical Engineering, 57:10 (Oct. 2010) pp. 2394-2401.
Witkowski et al., "In Vivo Estimation of Cardiac Transmembrane Current", Circulation Research 72:2 (Feb. 1993) pp. 424-439.
Yamada et al., "Electrophysiological Pulmonary Vein Antrum Isolation with a Multielectrode Basket Catheter is Feasible and Effective for Curing Paroxysmal Atrial Fibrillation: Efficacy of Minimally Extensive Pulmonary Vein Isolation", Heart Rhythm, 3:4 (Apr. 2006), pp. 377-384.
Yamada, "Pulmonary Vein Isolation with a Multielectrode Basket Cather"; Indian Pacing and Electrophysiology Journal, 7(2) (2006), pp. 97-109.
Zaman et al., "The Rotor Revolution Conduction at the Eye of the Storm in Atrial Fibrillation", Circulation (Dec. 2014), pp. 1230-1236.
Zhang et al., "Noninvasive Three-Dimensional Electrocardiographic Imaging of Ventricular Activation Sequence", Am J Physiol Heart Circ Physiol, vol. 289 (Aug. 5, 2005), pp. H2724-H2732.
International Search Report and Written Opinion for International application No. PCT/US2018/027607 mailed from the International Searching Authority dated Sep. 12, 2018 (16 pages.).
Anter et al., "High-Resolution Mapping of Scar-Related Atrial Arrhythmias Using Smaller Electrodes with Closer Interelectrode Spacing", Circulation 8:3 (Jun. 2015) 31 pages.
Arora et al., "Fundamentals of Intracardiac Mapping", Catheter Ablation of Cardia Arrhythimias (2006), pp. 107-134.
Avitall et al., "Maximal Electrogram Attenuation recorded from Mini Electrodes Embedded on 4.5-mm Irrigated and 8-mm Nonirrigated Catheters Signifies Lesion Maturation", Journal of Cardiovascular Electrophysiology 26:2 (Feb. 2015) pp. 1-11.
Balasundaram et al., "Tracking Rotors with Minimal Electrodes: Modulation Index Based Strategy", Circulation 8:2 (Apr. 2015) 34 pages.
Barnette et al., "Estimation of a 3-D Conduction Velocity Vector Fields from Cardiac Mapping Data", Computers in Cardiology, vol. 25 (Sep. 1998) pp. 605-608.
Bayly et al., "Estimation of Conduction Velocity Vector Fields from Epicardial Mapping Data", IEEE Transactions on Biomedical Engineering, 45:5 (May 1998) pp. 563-571.
Bayly et al., "Estimation of Conduction Velocity Vector Fields from 504-Channel Epicardial Mapping Data", Computers in Cardiology (Sep. 1996) pp. 133-136.
Benharash, "Quantitative Analysis of Localized Sources Identified by Focal Impulse and Rotor Modulation Mapping in atrial Fibrillation", Circulation (Jun. 2015) pp. 554-561.
Bharati et al., "The Conduction System of the Swine Heart", Chest 100:1 (Jul. 1991) pp. 207-212.
Bortone et al., "Unipolar Signal Modification as a Guide for Lesion Creation During Radiofrequency Application in the Left Atrium Prospective Study in Humans in the Setting of Paroxysmal Atrial Fibrillation Catheter Ablation", Circulation (Dec. 2013) pp. 1095-1102.
Bouman et al., "Structure and Function of the Sino-Atrial Node: A Review", European Heart Journal 7:2 (Feb. 1986) pp. 94-104.
Boyett et al., "The Sinoatrial Node, a Heterogeneous Pacemaker Structure", Cardiovascular Research 47:4 (2000) pp. 658-687.
Burch et al., "Chapter X the Development of Spatial Vectrocardiography", A History of Electrocardiography, Norman Publishing (Apr. 1990) pp. 235-248.
Cantwell et al., "Techniques for Automated Local Activation Time Annotation and Conduction Velocity Estimation in Cardiac Mapping", Computers in Biology and Medicine (Oct. 1, 2015) pp. 1-14.
Casella et al., "Feasibility of Combined Unipolar and Bipolar Voltage Maps to Improve Sensitivity of Endomycardial Biopsy", Circulation (Jun. 2015) 36 pages.
Chan et al., "The Effect of Ablation Length and Catheter Tip to Endocardial Orientation on Radiofrequency Lesion Size in the Canine Right Atrium", PACE 25:1 (Jan. 2002) pp. 4-13.
Damle et al., "Atrial and Accessory Pathway Activation Direction in Patients with Orthodromic Supraventricular Tachycardia: Insights from Vector Mapping", JACC 23:3 (Mar. 1, 1994) pp. 684-692.
de Bakker et al., "The Pathophysiologic Basis of Fractionated and Complex Electrograms and the Impact of Recording Techniques on Their Detection and Interpretation", Circulation (Apr. 2010) 3: pp. 204-213.
de Bakker et al., "Activation Mapping: Unipolar Versus Bipolar Recording", Cardiac Electrophysiology—From Cell to Bedside—Second Edition ISBN 0-7216-4941-6, pp. 1068-1078.
Deng et al., "Simulation of Biatrial Conduction via Different Pathways during Sinus Rhythm with a Detailed Human Atrial Model", Journal of Zhjiang University—Science B (Biomedicine & Biotechnology) Sep. 2012, 13(9): pp. 676-694.
Deng et al., "An Image-Based Model of the Whole Human Heart with Detailed Anatomical Structure and Fiber Orientation", Computational and Mathematical Methods in Medicine, vol. 2012; Jul. 2012, 16 pages.
Desai et al., "Two Phase Radiofrequency Catheter Ablation of Isolated Ventricular Endomyocardium", PACE vol. 14, (Jul. 1991), pp. 1179-1194.
Dubois et al., "Global and Directional Activation Maps for Cardiac Mapping in Electrophysiology", Computing in Cardiology (Sep. 2012), 39: pp. 349-352.
Faes et al., "A Method for Quantifying Atrial Fibrillation Organization Based on Wave-Morphology Similarity", IEEE Transactions on Biomedical Engineering, 49:12, (Dec. 2002), pp. 1504-1513.

(56) References Cited

OTHER PUBLICATIONS

Fedotov et al., "Methods for Increasing the Reliability of Coordinate Determination by the Location and Imaging Systems of Endocardial Electrodes", Biomedical Engineering 41:4 (Jul. 2007) pp. 145-149.
Fisher et al., "Three-Dimensional Electrogram Mapping Improves Ablation of Left-Sided Accessory Pathways", PACE vol. 15 (Dec. 1992) pp. 2344-2356.
Fitzgerald et al., "Comparative Psychometric Analysis of Vector and Isochrone Cardiac Activation Maps", IEEE Transactions on Biomedical Engineering 51:5 (May 2004) pp. 847-855.
Fitzgerald et al., "Estimation of Cardiac Conduction Velocities Using Small Data Sets", Annals of Biomedical Engineering, vol. 31 (Mar. 2003), pp. 250-261.
Fitzgerald et al., "Identification of Cardiac Rhythm Features by Mathematical Analysis of Vector Fields", IEEE Transactions on Biomedical Engineering 52:1 (Jan. 2005) pp. 19-29.
Gaudette et al., "Epicardial Velocity Estimation Using Wavelets", Computers in Cardiology 24 (Sep. 1997) pp. 339-342.
Gerstenfeld et al., "Detection of Changes in Atrial Endocardial Activation with Use of an Orthogonal Catheter", JACC 18:4 (Oct. 1991) pp. 1034-1042.
Gerstenfeld et al., "Evidence for Transient Linking of Atrial Excitation During Atrial Fibrillation in Humans", Circulation 86:2 (Aug. 1992) pp. 375-382.
Gornick et al., "Validation of a New Noncontact Catheter System for Electroanatomic Mapping of Left Ventricular Endocardium", Circulation (1999) 99: 829-835.
Gupta et al., "Rapid Ablation of Recurrent Atrial Flutter Using a Novel Ablation Catheter", The Journal of Innovations in Cardiac Rhythm Management (Nov. 2014), No. 5, pp. 1808-1812.
Haddad et al., "Novel Algorithmic Methods in Mapping of Atrial and Ventricular Tachycardia", Circulation (Jun. 2011), 29 pages.
Harrild et al., "A Computer Model of Normal Conduction in the Human Atria", Circulation Research (Sep. 29, 2000) 12 pages.
Horner et al., "Electrode for Recording Direction of Activation, Conduction Velocity, and Monophasic Action Potential of Myocardium", the American Physiological Society (Apr. 1997) pp. H1917-H1927.
Huang et al., "Evolution of the Organization of Epicardial Activation Patterns During Ventricular Fibrillation", Journal of Cardiovascular Electrophysiology (Dec. 1998) 9:12, pp. 1291-1304.
Ideker et al., "The Assumptions of Isochronal Cardiac Mapping", PACE, vol. 12 (Mar. 1989), pp. 456-478.
Irie et al., "Relationship Between Sinus Rhythm Late Activation Zones and Critical Sites for Scar-Related Ventricular Tachycardia: A Systematic Analysis of Isochronal Late Activation Mapping", Circulation (Apr. 2015) 32 pages.
Kadish et al., "Mapping of Atrial Activation with a Noncontact, Multielectrode Catheter in Dogs", Circulation (1999) 99: pp. 1906-1913.
Kadish et al., "Vector Mapping of Myocardial Activation", Circulation (Sep. 1986) 74:3, pp. 603-615.
Karney et al., "Quaternions in Molecular Modeling", Journal of Molecular Graphics and Modeling 25 (Jan. 2007) pp. 595-604.
Kay et al., "Measuring Curvature and Velocity Vector Fields for Waves of Cardiac Excitation in 2-D Media", IEEE Transactions on Biomedical Engineering 52:1 (Jan. 2005) pp. 50-63.
Kearsley, "On the Orthogonal Transformation Used for Structural Comparisons", Acta Cryst (Feb. 1, 1989) Section A45, pp. 208-210.
Kumar et al., "Unipolar Electrogram Morphology to Assess Lesion Formation During Catheter Ablation of Atrial Fibrillation Successful Translation into Clinical Practice", Circulation (Dec. 2013) pp. 1050-1052.
Lindsay et al., "Novel Directional Activation Map Using Local Propagation Between Adjacent Electrograms", Heart Rhythm 8:5 (May Supplement 2011) 2 pages.
Liu et al., "Three-Dimensional Imaging of Ventricular Activation and Electrograms from Intracavitary Recordings", IEEE Transactions on Biomedical Engineering 58:4 (Apr. 2011) pp. 868-875.
Liu et al., "Functional Characterization of the Crista Terminalis in Patients with Atrial Flutter: Implications of Radiofrequency Ablation", JACC 43:9 (May 5, 2004) pp. 1639-1645.
Mase et al., "Velocity Field Analysis of Activation Maps in Atrial Fibrillation a Simulation Study", World Congress (Sep. 2009, IFMBE Proceedings 25/IV, pp. 1014-1017.
International Search Report and Written Opinion for International Application No. PCT/US2018/027607 mailed from the International Searching Authority dated Sep. 12, 2018 (12 pages).

\* cited by examiner

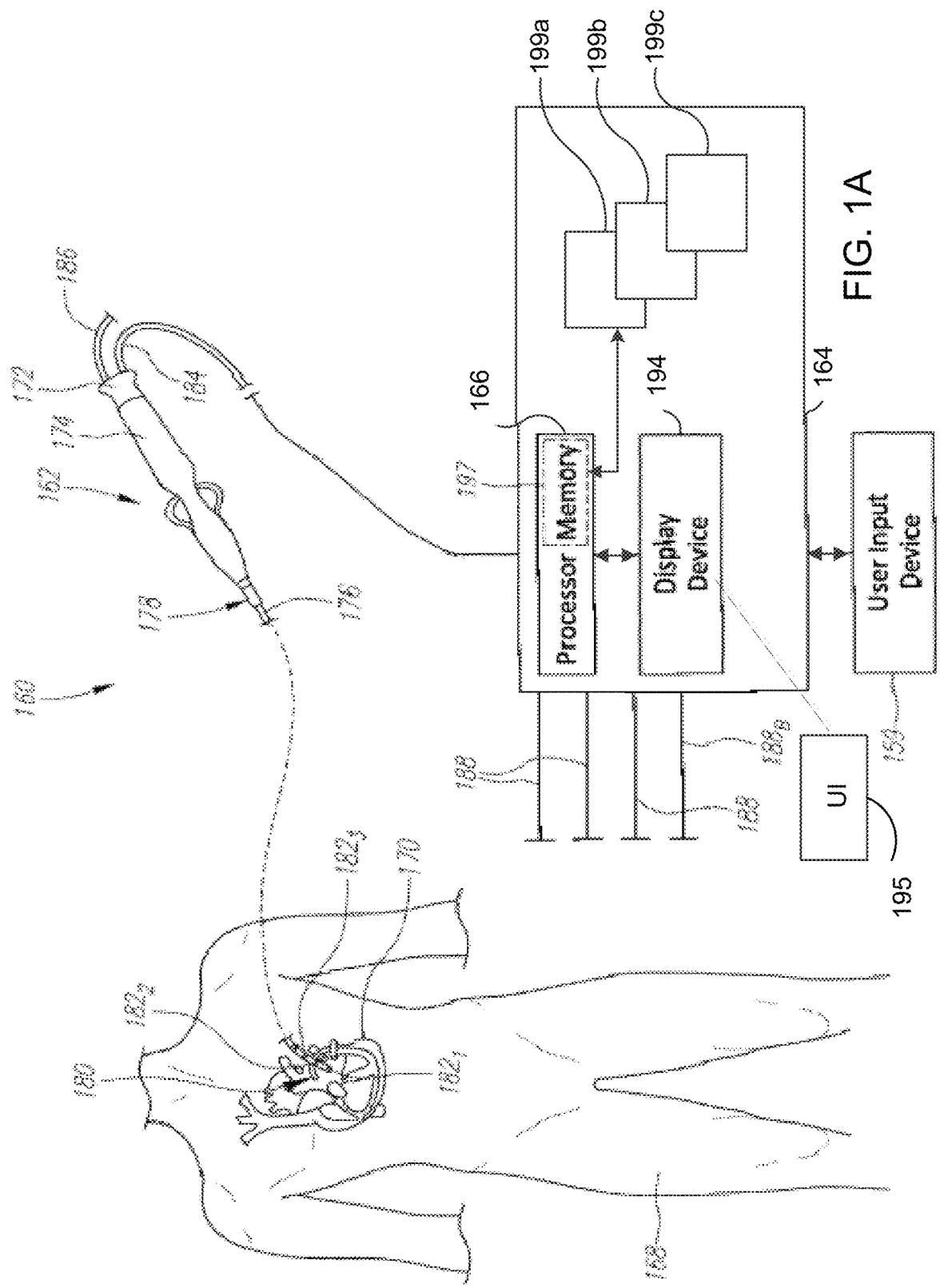

$$V_x = \frac{(V_A - V_B) + (V_C - V_D)}{2}$$

$$V_y = \frac{1}{2}[(V_A - V_C) + (V_B - V_D)]$$

US 10,758,137 B2

ORIENTATION INDEPENDENT SENSING, MAPPING, INTERFACE AND ANALYSIS SYSTEMS AND METHODS

CROSS REFERENCE TO RELATED APPLICATIONS

This application claims priority to and the benefit of U.S. provisional patent application No. 62/485,875, filed on Apr. 14, 2017, the disclosure of which is herein incorporated by reference in its entirety.

FIELD

In part, the disclosure relates generally to the field of vascular system and data collection and analysis relating thereto. More particularly, the disclosure relates, in part, to systems and methods to measure and analyze diagnostic information of interest based upon electrophysiology data.

BACKGROUND

Electrophysiology (EP) catheters are used in a variety of diagnostic, therapeutic, and/or mapping and ablative procedures to diagnose and/or correct conditions such as atrial or ventricular arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed and manipulated through a patient's vasculature to the intended site, for example, a site within a patient's heart. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. To position a catheter at a desired site within the body, some type of navigation may be used, such as using mechanical steering features incorporated into the catheter (or a sheath). In some examples, medical personnel may manually manipulate and/or operate the catheter using the mechanical steering features.

Various catheter designs, such as for example, spline-based catheters with an array of electrodes, can be used to perform voltage mapping relative to the cardiac system as noted above. Voltage mapping is an important clinical tool to evaluate arrhythmogenic myocardium and guides further diagnostic and therapeutic procedures. It is most often conducted using bipoles; however, the challenges of directional dependence and electrode spacing irregularity when using bipole-based signals can result in suboptimal data collection and erroneous signal processing.

In part, the present disclosure addresses these challenges and others, in part, by extending omnipolar-based systems and methods for use with voltage mapping and other tissue sensing related systems and methods as recited herein.

SUMMARY

The foregoing discussion is intended only to illustrate the present field and should not be taken as a disavowal of claim scope. The disclosure relates generally to applications of Orientation Independent Sensing (OIS) and Omnipolar mapping Technology (OT) to various system, device and method embodiments as recited herein. In one embodiment, the disclosure relates to systems and method of reducing one or more types of error associated with electrophysiology data acquired from a subject.

In part, the disclosure relates to a method of reducing one or more error types in cardiac system data obtained from a subject using a plurality of electrodes. The method includes defining an error reducing vector $\hat{m}$ by normalizing a differential electric field vector using a magnitude, wherein the differential electric field vector is a difference of a first electric field vector $E(t_j)$ and a second electric field vector $E(t_i)$, wherein $t_i$ and $t_j$ are electric field measurements in time, wherein $t_j > t_i$ and wherein the magnitude is $|E(t_j) - E(t_i)|$; determining a cardiac system parameter by performing a vector operation comprising operating, using an operator, upon (i) $\hat{m}$ or a vector perpendicular thereto $\hat{m}_\perp$ and (ii) a diagnostic vector, wherein the diagnostic vector is generated using measured cardiac electrogram signals to generate an output, wherein the output is a scalar output or a vector output; and displaying the output or information correlated with the output. In one embodiment, the method further comprises maximizing $|E(t_j) - E(t_i)|$.

In one embodiment, the operator is a dot product operator, wherein the diagnostic vector is $E(t)$, and wherein the output of $<\hat{m}, E(t)>$ is a scalar electrical field signal $E_m(t)$. In one embodiment, the method further comprises computing a peak to peak value of $E_m(t)$.

In one embodiment, the method further comprises determining a scalar voltage signal $Vm(t)$, wherein $Vm(t)$ comprises a product of k and $E_m(t)$, wherein k is an electrode spacing between the plurality of electrodes. In one embodiment, the method further comprises computing a peak to peak value of $V_m(t)$. In one embodiment, the operator is a dot product operator, wherein the diagnostic vector is $E(t)$, and wherein the output of $<\hat{m}\perp, E(t)>$ is a scalar electrical field signal $E_{m\perp}(t)$.

In one embodiment, the method further comprises determining one or more directional deviations between $\hat{m}$ and $\hat{a}$ and generating an alert when the one or more directional deviations exceeds a threshold, wherein the direction of $\hat{a}$ is an activation direction. In one embodiment, the threshold is an angular deviation between that ranges from about 15 degrees to about 20 degrees.

In one embodiment, the one or more error types include directionality-based errors and further comprising reducing directionality-based errors. In one embodiment, the method further comprises displaying one or more graphic user interface elements corresponding to or aligned with $\hat{m}$ relative to a 2D or 3D display of a cardiac tissue representation. In one embodiment, the method further comprises displaying the one or more graphic user interface elements corresponding to or aligned with $\hat{m}$ relative to one or more regions of detected cardiac tissue activation. In one embodiment, the method further comprises displaying a graphic user interface element that comprises a plurality of user selectable elements, wherein the user selectable elements comprise a plurality of triangular electrode cliques and a plurality of square electrode cliques.

In one embodiment, in response to user selection of one or more of the square electrode cliques or triangular electrode cliques, one or more waveforms associated with each clique selected is displayed. In one embodiment, the graphic user interface element is a guide diagram comprising a representation of an array of electrodes for a diagnostic catheter and one or more indicia, wherein the indicia corresponds to a parameter selected from the group consisting of a bipole voltage, a unipole voltage, a unipole wave form, a bipole waveform, an ablation gap, and an activation direction. In one embodiment, the indicium is a color and further comprising displaying a color coded legend comprising the color. Various other indicia may be used, without limitation, such as hatching, bolding, and other visual cues or graphical user interface elements. This broad range of possible indicia applies to all user interface and visual representations described or depicted herein.

In part, the disclosure relates to a method of determining diagnostic information for a subject using a plurality of electrode-based measurements. The method includes storing, in one or more electronic memory storage devices, one or more sets of electrophysiological (EP) data received with regard to one or more tissues of the subject, wherein the one or more sets comprise a first set of EP data; determining a set of electric field data from the first set of EP data, wherein the set of electric field data comprises a plurality of time varying electric field vectors; computing, for each pair of temporally adjacent electric field vectors of the plurality of time varying electric field vectors, a difference vector, wherein each difference vector has differential magnitude; identifying, from differential magnitudes of difference vectors, a relative extremum of the differential magnitudes, as a first differential magnitude; defining a first diagnostic parameter, m̂, wherein m̂ is proportional to or equal to the difference vector having the first differential magnitude; and displaying graphic user face element oriented along a direction of m̂. In one embodiment, the method further includes determining a second diagnostic parameter is (i) using a vector operator and m̂ or (ii) a vector correlated with m̂ or derived therefrom.

In part, the disclosure relates to a method of generating a reference signal suitable for comparison to one or more cardiac tissue measured signals. The method includes selecting a clique of connected unipoles in a non-linear arrangement; converting combination of selected unipoles and associated bipoles to electric field components; and converting electric field components to electrical potential signals $V_x$ and $V_y$, wherein x and y are axes of catheter reference frame.

In one embodiment, the method further includes normalizing $V_x$ and $V_y$ signals to generate a direction independent signal. In one embodiment, the method further includes filtering the direction independent signal to generate a filtered direction independent signal, wherein the filtered signal is directionally independent. In one embodiment, the step of filtering comprises one or more steps selected from the group consisting of reducing an error associated with detection of depolarizations, low pass filtering, differentiating, and signal thresholding.

In one embodiment, the method further includes processing the filtered direction independent signal using a refractory period of cardiac tissue, a noise floor, and a zero-crossing detector to detect polarization events in the filtered signal. In one embodiment, the normalizing step comprises determining a Euclidean magnitude. In one embodiment, the step of converting the combination of selected unipoles and associated bipoles is performed by performing a least squares fit. In one embodiment, the method further includes measuring a plurality of electrical signals from cardiac tissue during atrial fibrillation and characterizing spatial coherence of a vector field derived using the cardiac system parameter.

In one embodiment, the step of characterizing is performed using a coherence or entropy measurement of one or more vectors of the vector field. In one embodiment, the step of characterizing is performed by coherence filtering Vmax values on a per cycle basis and comparing filtered results for each cycle to exclude inconsistent regions between different cycles.

In one embodiment, one or more methods include identifying ablation line gaps. In one embodiment, one or more methods include mapping a scar border, isthmus within scar or locus. In one embodiment, one or more methods include assessing an atrial substrate, in regular sinus rhythm and also during atrial fibrillation. In one embodiment, one or more methods include locating a reentrant entrance site or exit site.

Although, the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation and steps from various methods can be combined without limitation. Notwithstanding the foregoing and the other disclosure herein, embodiments disclosed herein may also be applied in the context of bipolar based systems and methods as applicable.

Other features and advantages of the disclosed embodiments will be apparent from the following description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a diagrammatic view of a system for generating surface models, mapping electrophysiological information thereon, and/or providing user interfaces, diagnostic information, electrophysiological vector representations, and positional information.

DETAILED DESCRIPTION

Overview

Figure 1B:
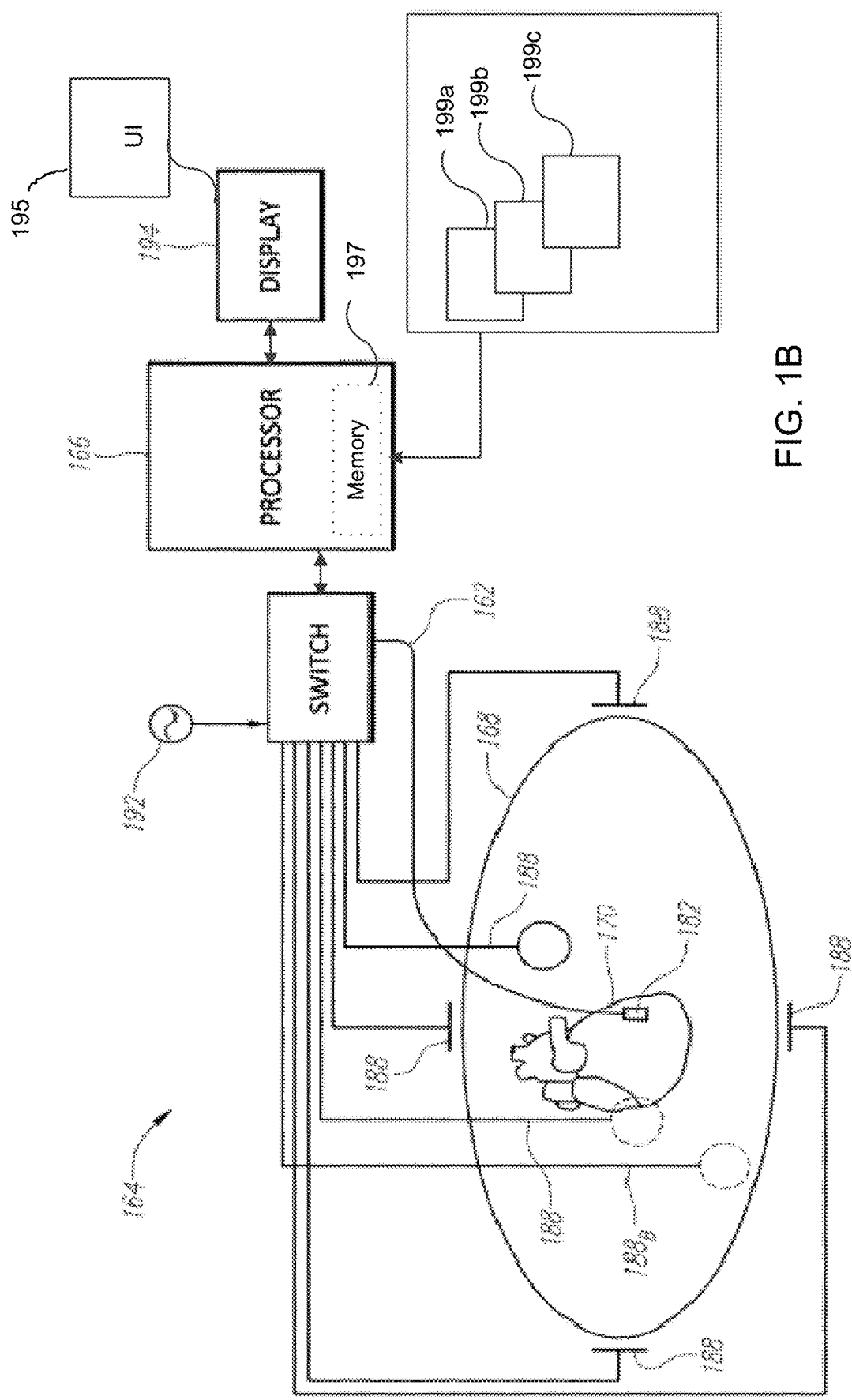
FIG. 1B is simplified diagrammatic and schematic view of the system illustrated in FIG. 1A.

The disclosure relates generally to applications of Orientation Independent Sensing (OIS) and Omnipolar mapping Technology (OT) to various system, device, and method embodiments such as voltage mapping and others as recited herein. Voltage mapping is an important clinical tool to evaluate arrhythmogenic myocardium and guides further diagnostic and therapeutic procedures. In part, the disclosure provides new analytical tools and data representations based on OIS technology to enhance voltage mapping and other methods. Additionally, systems and methods suitable for supporting OIS and OT systems and methods are disclosed.

Further, OIS and OT implementations that provide end user interfaces, diagnostic indicia and visual displays generated, in part, based on measured data or derived from measured data are also disclosed. In general, the disclosure relates to implementations and features that generate, collect, and process electrophysiological information (each of the terms "electrophysiology" and "electrophysiological" will hereinafter be referred to as "EP"). Similarly, the terms "OIS" and "OT" are used interchangeably herein unless otherwise specified.

Embodiments disclosed herein also apply optimization techniques to determine the greatest voltage difference (or a relative extremum of differential magnitudes/values thereof) of a local electric field associated with an electrode-based diagnostic procedure and a vector representation thereof which is introduced in more detail below as m̂ (or m-hat) along with variations and extensions thereof to other diagnostic vectors such as other OT metrics and parameters. Such a vector representation and other vectors derived from and correlated with are also described herein and are generally referred to as diagnostic vectors. The diagnostic vectors can provide directional and positional feedback as well as other visual indicia to an end user. For example, a display of such diagnostic vectors can be used to guide an end user manipulating a catheter to a location of interest such as a region of tissue activation in the heart.

In addition, the disclosure also includes embodiments suitable for generating a reference trigger that reduces one or more error types including directional effects and common mode far-field noise. The reference trigger remains directionally independent even if determined using bipoles. The implementation of a directionally independent reference trigger can result in increased reliability and consistency. The foregoing and other embodiments and design features of various systems, methods, and devices are described herein. Prior to considering these in more detail, it is informative to consider how they relate to various OIS and OT implementations.

OIS describes one or more sensing methods including methods of determining myocardial activation direction that is insensitive to catheter orientation. Currently, myocardial activation is measured by traditional bipoles created from neighboring electrodes, which span a limited number of directions due to the limited number and spacing of physical electrodes. By combining the information from all signals of a clique (collection of immediately adjacent electrodes used to derive EP characteristics) as an omnipole, an 'effective bipole' can be calculated. This combination avoids the limitation on direction imposed by physical bipoles.

Further, the ability to calculate a bipole in any direction allows for the determination of the largest peak-peak voltage value regardless of catheter (bipole) orientation. Previously, orienting bipoles in the direction of the E-field was required to yield the largest peak-peak voltage, and was not possible to achieve in most circumstances. As a result, the features described herein with regard to OIS, m-hat, and others offer clear improvements relative to established methods.

Cardiac EP mapping today primarily uses electrograms (EGMs). The EGMs are typically bipolar and obtained from electrode pairs. Unipolar EGMs may contain far-field information and less stable baselines that make them less attractive for mapping purposes. A feature of the unipolar signal that makes it useful for mapping is the fact that its morphology and amplitude are independent of catheter orientation. Amplitudes and morphology of bipolar EGMs are dependent on the wave front and relative orientation of the electrode pair from which they are calculated and hence depend on the orientation of the catheter.

EP information may also be elicited by pacing a tissue or organ and observing the resulting spread of depolarization from immediately adjacent to the site where capture occurs. These observations are difficult with current technology because of pacing artifacts and other errors but directional information in the form of or derived from voltage or electric filed information, as described herein, can be used to reduce errors or remove degrees of uncertainty or ambiguity. For example, vectors or paths indicative of direction of activation or a direction opposite the direction of activation can advantageously be used as part of a user interface to facilitate positioning of a diagnostic electrode-based catheter.

A guide diagram or interface such as a color map or other user interface overlay or component can be used as a diagnostic tool to guide targeted ablation, data collection, and other procedures can be initiated once the catheter has been positioned relative to its target location. A given color map can also be referred to an indicia map or a map or mapping generally. A given color map can be represented as an indicia map with hatching, shading, dotted and patterned lines, and other visual cues to provide a user with a visual awareness of the features of any such map. The use of a schema or rubric to define the spatial relationship between electrodes in a catheter can be shown alone or with useful indicia and a legend to guide an end user. Further, such a representation of electrodes can be used to visualize and measure the orientation and patterns of vectors in a vector field. With such vectors being derived using EP measurements and the extremal vector techniques described herein, details relating to spatial coherence of such vectors as determined by entropy-based analysis can be advantageously used during AF as discussed in more detail herein.

In addition, directional ambiguity in terms of how to decide where to position a catheter to accurately target a specific region of activation can be advantageously reduced or constrained or guided using m-hat, color maps, user interface indicia and other information when presented to a catheter operator. The guiding of an end user and the representation of m-hat and other user interface features can be presented in one or more user interface windows as described in more detail below. For example, end user guidance can be provided by outputting m-hat or other indicia relative to one or more views of a geometric surface model generated using EP measurements and/or EGMs.

With respect to bipoles, the dependence on orientation results in inconsistently measured amplitudes and morphology-based measurements like activation times as a result of directional and other errors. In turn, the errors also impact derived quantities like scar boundaries, activation direction, and conduction velocity. Generally, these types of unwanted effects and error propagation between analytic modules that rely on previously measured or generated data are generally referred to as errors or error types.

Given the unwanted effects associated with orientation and directionality issues, directionality-based errors is used as a category to reference these errors types and others. In part, the use of m-hat, direction independent reference triggers and other features disclosed herein support methods of reducing various error types.

In one embodiment, the methods, systems, and devices disclosed herein may be used without a navigational system and thus have wide applicability in EP recording systems adapted for OT catheters. Further, determining a scalar E-field or voltage EGM signals can be performed strictly within the catheter coordinate frame. The resulting scalar signals and peak to peak levels do not need navigation (electrode position) information.

In addition, the foregoing overview of various embodiments can also be combined with or otherwise form part of a system or method to perform one or more of the following: identifying ablation line gaps; map scar borders such as ventricular tachycardia (VT) scar borders; identify low voltage channels, and isthmus within a scar; assessing an atrial substrate; and locating reentrant entrance or exit sites. With the foregoing to provide context and outline of some of the embodiments to follow, it useful to consider some system embodiments and catheter related features to provide further context.

Exemplary System Features and Embodiment Details

FIG. 1A illustrates one embodiment of a system 160 for mapping EP information corresponding to an anatomic structure onto a multi-dimensional (e.g., three-dimensional) geometry surface model (GSM) of the anatomic structure. The system 160 comprises, among other components, a medical device 162 and a data collection and analysis systems 164 suitable for collecting EP data and other data as described herein from a subject and to generate outputs that include data displays, user interfaces, and other OT related features disclosed herein. In one embodiment, the medical device 162 comprises a catheter, and system 164 comprises, in part, a processing apparatus 166.

The processing apparatus 166 may include one or more apparatus, devices, and machines for processing data, signals and information, including by way of example a programmable processor, a computing device such as a computer, or multiple processors or computers. The apparatus can include, in addition to hardware, code that creates an execution environment for the computer program in question, e.g., code that constitutes processor firmware, a stack, a data management system, an operating system, one or more user interface systems, or a combination of one or more of them.

Further, the processing apparatus 166 can include machine readable medium or other memory that includes one or more software modules for displaying a graphical user interface such as an interface for system 160. The processing apparatus 166 can exchange data such as monitoring data or other data using a network, which can include one, or more wired, optical, wireless or other data exchange connections.

The processing apparatus 166 may include a server computer, a client user computer, a control system, a diagnostic system such as, for example, a cardiac diagnostic system, a microprocessor or any device capable of executing a set of instructions (sequential or otherwise) that specify actions to be taken by that processing apparatus 166 Further, the term "processing apparatus" shall also be taken to include any collection of computing devices that individually or jointly execute a set (or multiple sets) of instructions to perform any one or more of the software features or methods or operates as one of the system components described herein.

The processing apparatus 166 may take the form of an electronic control unit, for example, that is configured to obtain a GSM of the cardiac structure, and to construct an EP map corresponding to the cardiac structure using data collected by, for example, the catheter 162. The catheter 162 is configured to be inserted into a patient's body 168, and more particularly, into the patient's heart 170. The catheter 162 may include a cable connector or interface 172, a handle 174, a shaft 176 having a proximal end 178 and a distal end 180 and one or more sensors 182 (e.g., 182₁, 182₂, 182₃) mounted in or on the shaft 176 of the catheter 162. In one embodiment, the sensors 182 are disposed at or near the distal end 180 of the shaft 176. The connector 172 provides mechanical, fluid, and electrical connection(s) for cables, such as, for example, cables 184, 186 extending to system.

The sensors 182 mounted in or on the shaft 176 of the catheter 162 are electrically connected to system 164, and the processing apparatus 166 thereof, in particular. The sensors 182 may be provided for a variety of diagnostic and therapeutic purposes including, for example and without limitation, EP studies, pacing, cardiac mapping, and ablation. In an embodiment, one or more of the sensors 182 are provided to perform a location or position sensing function such as guidance relative to one or more activation regions wherein activation can occur at different points in time.

Accordingly, in such an embodiment, as the catheter 162 is moved along a surface of the cardiac structure and/or about the interior thereof, the sensor(s) 182 can be used along with the display outputs and vectors or line segments described in more detail with m-hat and its associated cohort of other diagnostic vectors and OT metrics, operators and parameters.

In one embodiment, system 164, and the processing apparatus 166 thereof, in particular, is configured to obtain a GSM of the cardiac surface (or at least a portion thereof), and to map EP information corresponding to that cardiac structure onto the GSM. Examples of GSMs are shown in the graphical user interface representations in FIGS. 13, 15, and 16 which are discussed in more detail herein. The processing apparatus 166 is configured to use, at least in part, data (location data and/or EP data/information) collected by the catheter 162 in the construction of one or both of a GSM and an EP map and to other perform the various OT related mapping and other methods and features disclosed herein.

In an embodiment, wherein system 164 is configured to construct the GSM, system 164 is configured to acquire location data points collected by the sensor(s) 182 corresponding to the cardiac structure. System 164 is configured to then use those location data points in the construction of the GSM of the cardiac structure. System 164 is configured to construct a GSM based on some or all of the collected location data points. System 164 is configured to function with the sensor(s) 182 to collect location data points to support the directionally independent voltage mapping and other data analysis and user interface features disclosed herein. In such an embodiment, system 164 may comprise an electric field-based system, such as, for example, the EnSite NavX™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. Another exemplary system 164 is the EnSite Precision™ system, which uses both impedance-based and magnetic based localization.

As part of the user interface designs and other analysis and data processing and display features disclosed herein, the GSM representation is depicted relative to one or more line segments, scalar values, or vectors. These geometric, directional, scalar values, alone or in combination are designed to be indicative of a direction of heart tissue activation or otherwise inform the user of a path or direction of movement to iteratively test via catheter rotation and positional changes to reach of target position of interest.

With reference to FIG. 1B, in addition to the processing apparatus 166, system 164 may include, among other possible components, a plurality of patch electrodes 188, a multiplex switch 190, a signal generator 192, and a display device 194. In another exemplary embodiment, some or all of these components are separate and distinct from system 164 but that are electrically connected to, and configured for communication with, system 164.

The processing apparatus 166 may comprise a programmable microprocessor or microcontroller, or may comprise an application specific integrated circuit (ASIC). The processing apparatus 166 may include a central processing unit (CPU) and an input/output (I/O) interface through which the processing apparatus 166 may receive a plurality of input signals including, for example, signals generated by patch electrodes 188 and the sensor(s) 182, and generate a plurality of output signals including, for example, those used to control and/or provide data to, for example, the display device 194 and the switch 190.

The processing apparatus 166, such as for example through memory 197, includes or accesses one or more software modules or programs 199a, 199b, and 199c, such as a reference trigger generation or processing module, an optimization module suitable to select max, min, and relative extremum values from electric field and potential values, an m-hat determination module, vector operation modules, GSM display modules, m-hat display modules, user catheter guidance modules, activation region display modules, user interface modules, voltage mapping modules and other software modules. The modules 199a, 199b, and 199c can be subsets of each other and arranged and connected through various inputs, outputs, and data classes. Also, three exemplary modules 199a, 199b, and 199c are depicted in FIG. 1A, any suitable number of modules can be installed or access by system 160 various embodiments.

The processing apparatus 166 may be configured to perform various functions, such as those described in greater detail above and below, with appropriate programming instructions or code (i.e., software 199a, 199b, and 199c). Accordingly, the processing apparatus 166 is programmed with one or more computer programs encoded on a computer storage medium for performing the functionality described herein. These functions can include generating one or more user interface (UI) components suitable for display on the display device. The user interface components can also be displayed on the user input device to the extent it includes a touch screen or other display. One or more of the software modules or components thereof can be used to implement the user interface components described and depicted herein. These interfaces can include a select all feature (SA) by which all the square electrodes or all of the triangular electrodes in an array can be selected for displaying EP signals and related parameters relative thereto.

With the exception of the reference patch electrode 188B called a "belly patch," the patch electrodes 188 are provided to generate electrical signals used, for example, in determining the position and orientation of the catheter 162. In one embodiment, the patch electrodes 188 are placed orthogonally on the surface of the body 168 and are used to create axes-specific electric fields within the body 168.

In one embodiment, the sensor(s) 182 of the catheter 162 are electrically coupled to the processing apparatus 166 and are configured to serve a position sensing function. More particularly, the sensor(s) 182 are placed within electric fields created in the body 168 (e.g., within the heart) by exciting the patch electrodes 188.

In part, the disclosure uses electrodes on diagnostic catheters to derive local "pseudo bipolar", "equivalent bipole", direction independent reference signals, diagnostic vectors, or "omnipolar" signals that are catheter orientation independent and are free of low-frequency noise and far-field effects. The electrodes can be located on a diagnostic or other catheter or in some embodiments can be located on multiple catheters where electrodes on the catheters are located near or adjacent each other. Furthermore, the equivalent bipolar EGMs so derived possess characteristic shapes and relationships that reflect physiologic and anatomic directions which enable better contact maps by virtue of more consistent activation timing directions.

Figure 2A:
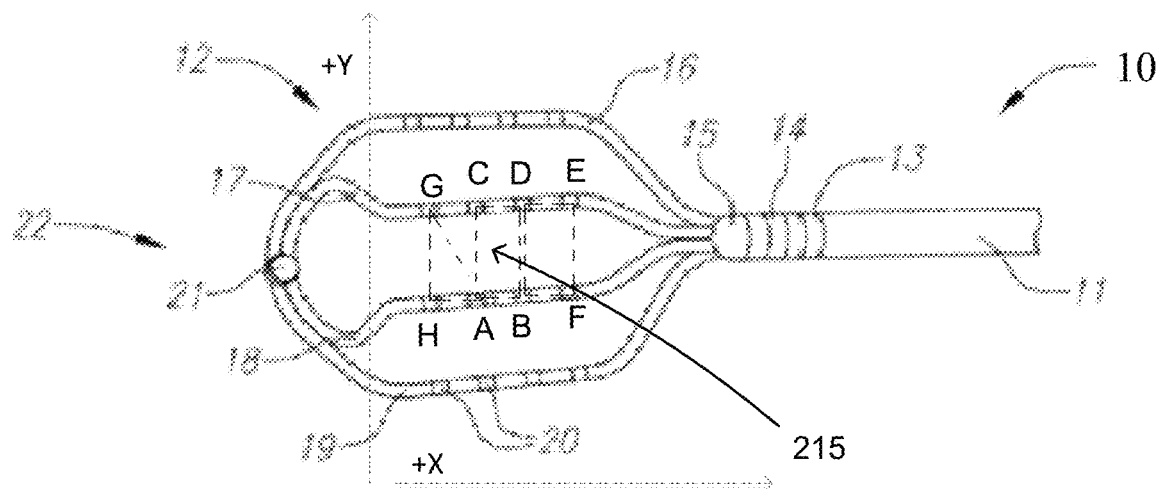
FIG. 2A is an isometric view of one embodiment of an exemplary catheter having electrodes groupable into square and triangular cliques according to an illustrative embodiment.

FIG. 2A shows an embodiment of a diagnostic catheter that can be used for mapping and data collection applications as described herein. Various diagnostic catheters that include an array of electrodes or other electrode configurations can be used to implement the embodiments disclosed herein. In one embodiment, the diagnostic catheter is a high density (HD) catheter such as an HD grid catheter. The Advisor™ HD Grid Mapping Catheter (commercially available from St. Jude Medical, Inc.) is an exemplary HD catheter suitable for use in various embodiments. Similarly another embodiment includes an ablation catheter with segmented electrodes with a distal ablating electrode with proximal segmentation or vice versa enabling tetrahedral or multiple triangular clique formations.

Examples of other types of ablation and/or diagnostic catheters that can be used for collecting data as described herein are disclosed in U.S. Patent Publication No. 2016/0045133 entitled "Utilization of Electrode Spatial Arrangements for Characterizing Cardiac Conduction Conditions," the contents of which are incorporated herein by reference in their entirety. Generally, any suitable diagnostic catheter can be used as applicable with any given embodiment disclosed herein.

FIG. 2A illustrates one embodiment of a diagnostic catheter 10 comprising a catheter body 11 coupled to a paddle 12. The catheter body 11 can further comprise a first body electrode 13 and a second body electrode 14. The paddle 12 can comprise a first spline 16, a second spline 17, a third spline 18, and a fourth spline 19 that are coupled to the catheter body 11 by a proximal coupler 15 and coupled to each other by a distal connector 21 at a distal end of the paddle 22. In one embodiment, the first spline 16 and the fourth spline 19 can be one continuous segment and the second spline 17 and the third spline 18 can be another continuous segment.

In other embodiments, the various splines can be separate segments coupled to each other. The plurality of splines can further comprise a varying number of electrodes 20. The electrodes in the illustrated embodiment can comprise ring electrodes evenly spaced along the splines. In other embodiments, the electrodes can be evenly or unevenly spaced and the electrodes can comprise point or other types of electrodes.

In FIG. 2A, a representative group of catheter electrodes A, B, C, D, E, F, and G are depicted with regard to an exemplary catheter 10. The central clique of electrodes 215 includes electrodes A, B, C, and D. In one embodiment, the central clique defines a square with each vertex corresponding to one of A, B, C, and D as shown by the dotted lines for central clique 215. Although applicable to other four electrode groupings, the four electrode square (or rectangle) clique defined by A, B, C, and D can also be analyzed by deconstructing the ABCD grouping into four triangular electrode cliques. With regard to FIG. 2A, the four triangular electrode groupings or cliques of center clique 215 as defined by their vertices are ABD, ACD, CAB, and CDB. In this way, there are four triangular electrode groupings one for each of the four vertices of the square.

Each vertex forms a right angle with two orthogonal sides of the square or rectangular clique for four electrodes. As shown, by the dotted lines, an exemplary triangular grouping is also shown by electrodes GHA to the left of central clique 215. Measurements obtained from the various electrodes can be used to determine various parameters of interest such as Emax or Vmax. The E field trajectory over a depolarization typically forms a loop, which can be shown in a two or three-dimensional graph such as those shown in FIGS. 3, 14, and 15. E field derived loops, such as for example those derived using a least squares approach, preferably merge information from all possible bipoles of a clique. Generally, when determining Emax (or Vmax), the determined values will exceed the amplitudes of individual constituent bipoles. This relationship between the amplitudes of their respective constituent bipoles is true with respect to measurements using triangular cliques as discussed below.

Still referring to FIG. 2A, and the central clique formed by electrodes A, B, C, and D, in light of the discussion of omnipoles above, it is useful to consider the electrode cliques with regard to bipoles. There are six possible bipoles, four from the sides of the square (e.g. A-B, C-D, A-C, and B-D) and two diagonals (e.g. A-D and C-B). In general, in the context of using a mapping system (such as, for example, an Ensite™ Velocity mapping system) to assess voltages from a single or rectangular square clique, the foregoing six bipoles would be present for each group of four electrodes.

Figure 2B:
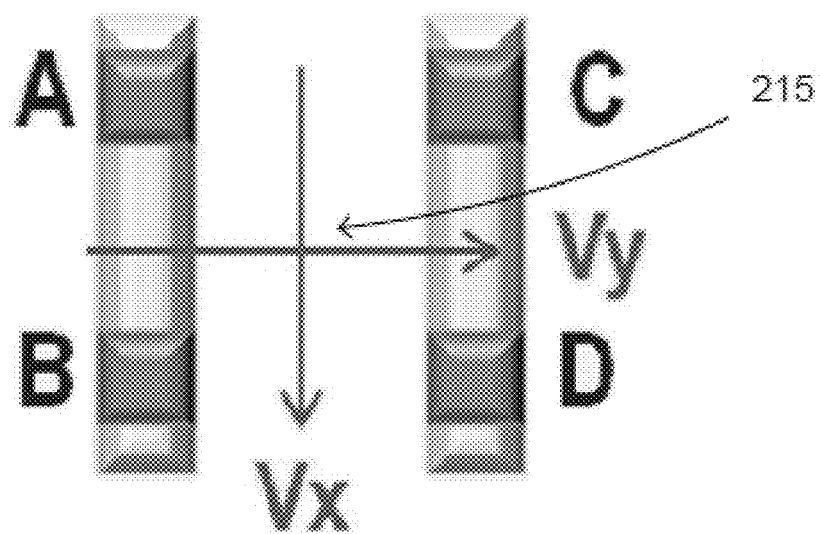
FIG. 2B is a zoomed in view of four electrodes suitable for grouping as square or triangular cliques relative to a catheter reference frame for reference trigger generation and relationships for determining directional bipole signals along catheter axes.

To provide further context, although depicting a different diagnostic electrode-based catheter, in FIG. 2B, an idealized catheter coordinate frame that includes axes for the +x and +y directions, respectively. These reference frame axes for bipole direction is also shown in FIG. 2A. The clique of four electrodes A-D is shown for a subset of a catheter's electrodes to provide information relating to bipoles. In particular, the bipole potential equations and directionality of $V_x$ and $V_y$ are displayed. These equations can be written in the following form:

$$V_x = \frac{(V_A - V_B) + (V_C - V_D)}{2}$$

$$V_y = \frac{1}{2}[(V_A - V_C) + (V_B - V_D)]$$

Methods of determining $E_{max}$ (or equivalently Vmax) are expected to yield from E field loops voltage values which are equal to or greater than those of the bipoles making up a clique. However, this is strictly true only for triangular cliques. For square cliques there is an averaging effect of opposing side bipoles as seen in the equations for $V_x$ and $V_y$ above and in FIG. 2B. Under certain scenarios, $E_{max}$ is constrained to be greater than or equal to the peak-to-peak E fields of the two adjacent sides and their diagonal. For example, the foregoing $E_{max}$ constraint applies to isosceles right triangular cliques and least squares solutions to E(t). When expressed as a maximal bipole voltage, $V_{max}$ will also be greater than or equal to its constituent side bipoles as well as the scaled for excess length voltage of the constituent diagonal.

In light of the various diagnostic features and embodiments disclosed herein, it is also informative to consider methods of enhancing spatial resolution in the context of electrode cliques. If a single bipole were to be substantially greater in peak-to-peak voltage than any of its neighboring bipoles, then the four electrode square clique approach would map this with mid-level values as mentioned above to each of the two adjacent squares. If instead, the triangular clique method is used, this same large single bipole voltage would be mapped exactly to four large values belonging to the triangular cliques that are just 1 mm each side of the bipole. As a result, the triangular clique approach faithfully provides the single bipole's high value while achieving greater spatial resolution by mapping that high value to a region of half the surface area located precisely on both sides of his large bipole.

Figures 12A, 12B:
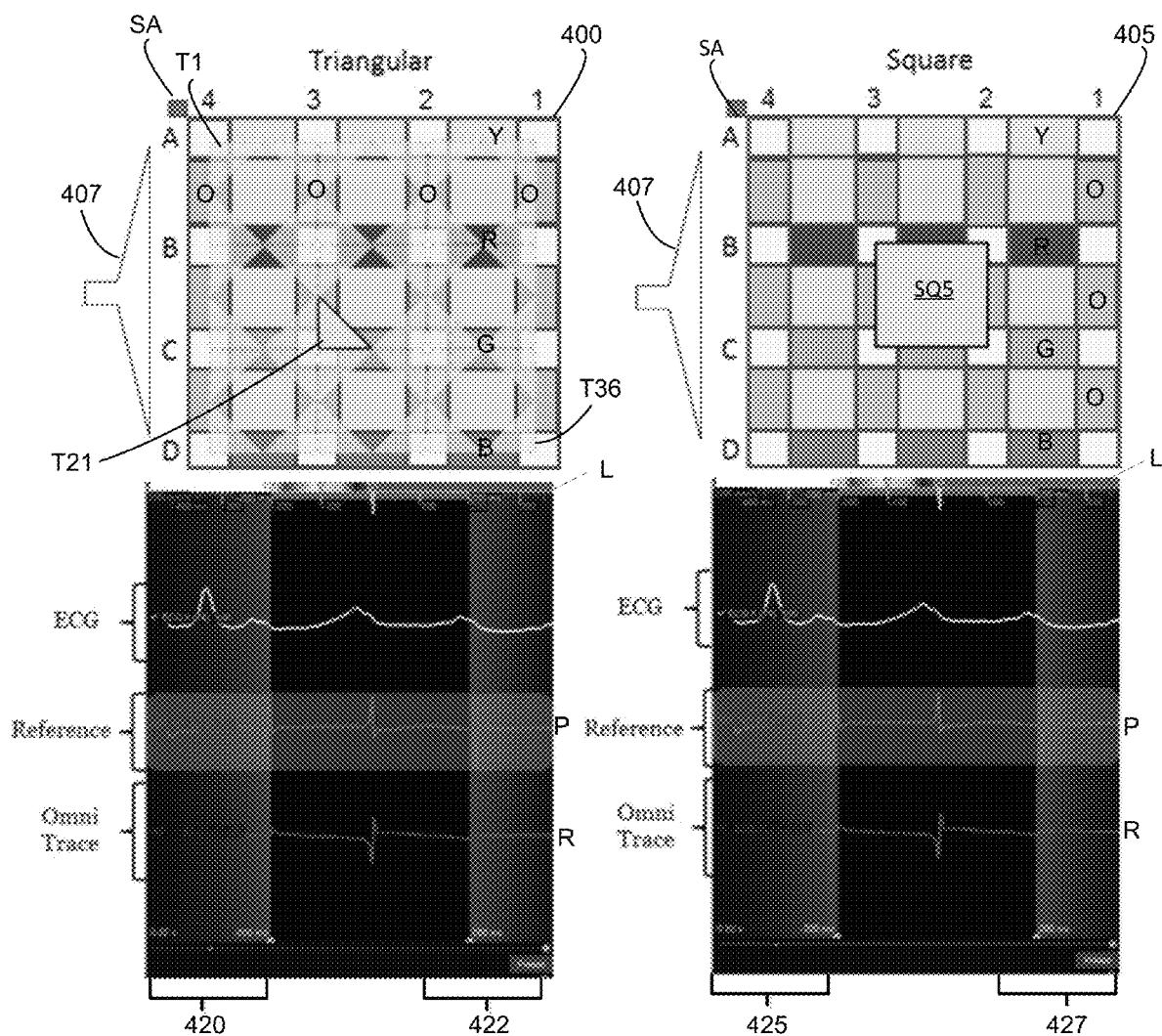
FIGS. 12A-12F are user interface components that include a guide user interface and waveforms displayed in response to the user selection of various combinations of square and triangular cliques.

From this example, dividing the catheter electrode groupings such that an array of triangles is defined provides a method to increase granularity and signal resolution. The benefits of such an approach have been empirically validated and shown to improve spatial resolution. Specifically, the use of triangular cliques yields an improved spatial resolution to relative to the use of square cliques with regard to applications disclosed herein. In one embodiment, as shown in FIG. 12B discussed in more detail herein, groups of triangles in the array define repeating square groupings that are rotated 45 degrees or another angle of rotation relative to the square clicks of the catheter.

Although the diagonal bipoles have longer interelectrode spacings, and longer spacings generally imply greater voltages, they are not always larger than any of the sides. Decomposing an OT square clique into four maximal bipole (omnipole) voltage values and outputting them as part of a user interface display as four triangular omnipole voltages with each next to its bipole constituents is an embodiment of the disclosure. Now in each of these four cases, the omnipole peak-to-peak value will meet or exceed the greatest constituent bipole. This decomposing and display approach is in contrast to showing one square omnipole next to its six constituent bipoles.

In one embodiment, according to one method or system implementation, two bipole waveforms and the corresponding omnipole "maximal bipole" voltage waveform are displayed using one or more user interfaces. Accordingly, in one embodiment, in which a triangular array-based approach is implemented, instead of obtaining nine voltage values (centered in each of the nine squares that result from a diagnostic catheter having a 4×4 array of electrodes) at 4 mm spacings with respect to each other, 36 OT voltage values are obtained in an array, but with only 2 mm interelectrode spacings. The spatial resolution of voltage maps thereby improves over the 4 mm square clique approach. Further, undesirable voltage reductions are avoided when bipole orientations do not align with activation directions. This latter problem contributes to the generation of splotchy voltage maps. As a result, the use of an array of triangular cliques to address such noise and resolution related issues, is desirable.

OIS and OT based technology provide for voltage mapping methods, systems and devices. As discussed with regard to FIGS. 3 and 4, wave propagation models and electric field loop analysis allows for various OT metrics and applications thereof to be generated. These metrics and other related tools and information can extend existing techniques based on EGM signal analysis and monitoring. For example, among measures for EGM signal amplitude, the most commonly used is peak-to-peak voltage (PP or $V_{pp}$). With the advent of OT friendly catheters such as HD Grid, new measures of local tissue can be derived such as the direction of the maximal bipole voltage or the EGM signal perpendicular to that direction. The extensions in the form of operators, parameters, vectors, and associated user interface components and reference signals offer advantages relative to existing EP measurements and data analysis. To provide context, additional disclosure follows to establish various OT metrics and related data and applications with regard to FIG. 3 and FIG. 4.

Figure 3:
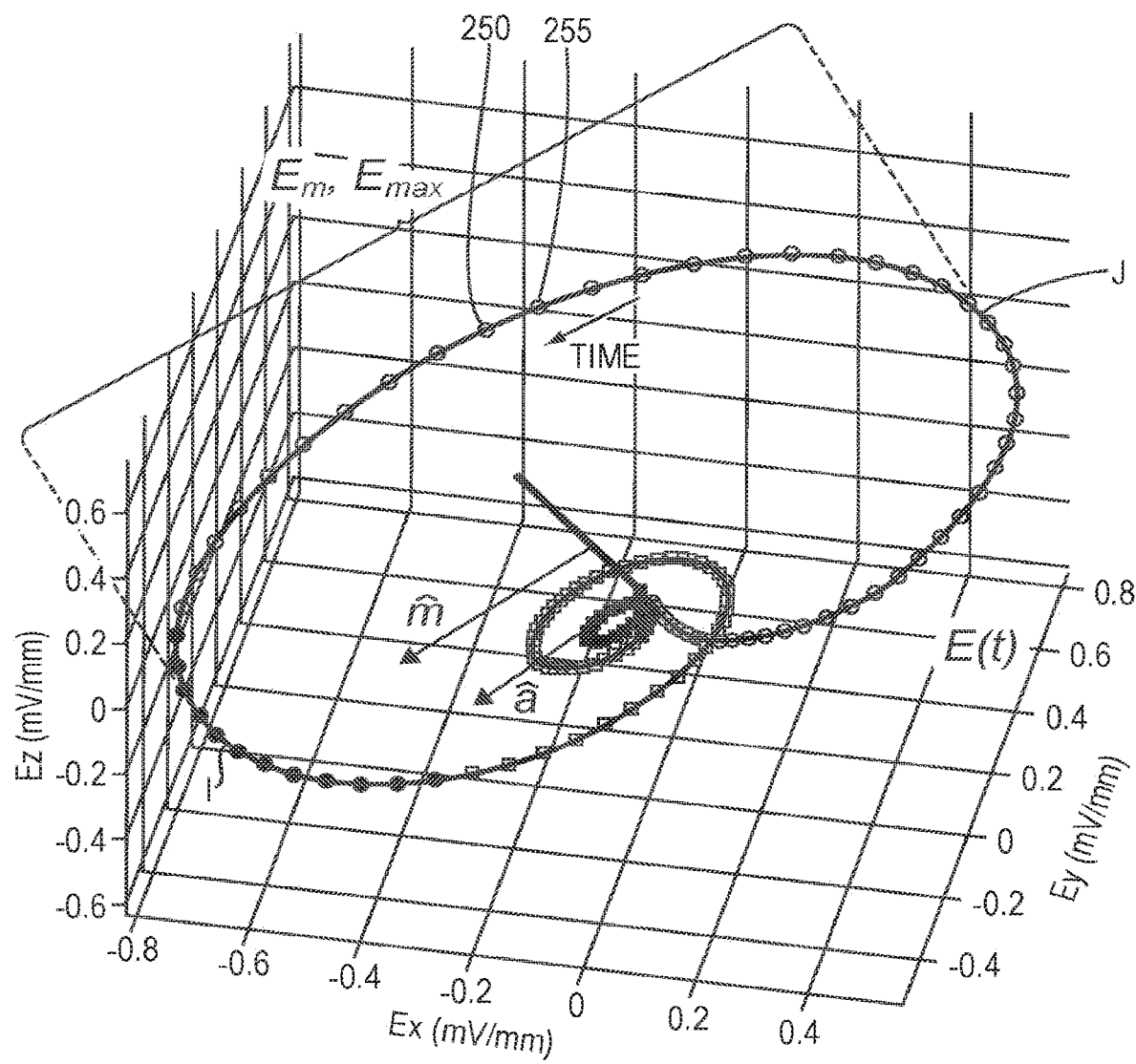
FIG. 3 is a graph of an E(t) loop in 3D that includes m-hat oriented in the direction of maximum (or relative extremum) peak-peak voltage and electric field magnitude.

FIG. 3 is a graph of an E(t) loop in three-dimensions. With each depolarization, the local electric field vector, E, sweeps out a loop like trajectory governed by anatomic and physiologic factors adjacent to these arrangements of electrodes. Two dimensional electrode arrangements allow the resolution of Et, the "tangent bipole vector", to which wave propagation principles can be applied and can be used to introduce a scalar version of Et along the unit activation direction â and identify this electrogram signal as Ea (not shown).

As part of the analysis of the E-loop data, it is useful to focus on the portions of a given E-loop that contain the most information. These informationally dense parts of the loop correspond to portions of the loop in which spacing between the adjacent electric field data point values in the loop is largest. These times or data points correspond to when the E-field changes most rapidly. Accordingly, it is at these time or data points that are least influenced by various error types such as noise, artifacts and other unwanted effects. In light of the foregoing, it is advantageous to develop a diagnostic and error reducing mechanism to extract the most useful information from collected electrogram data and other EP data.

The desire to find the times, unit direction vector, and E-field "span" associated with when the magnitude of the vector $E(t_j)-E(t_i)$ is greatest are all items of interest that can be incorporated in the OT metrics described herein. The span across the whole loop (not just intervals where it changes greatly) includes the curve segment between endpoints A and B is of interest in various embodiments. This span is the 2-D or 3-D equivalent of peak-to-peak for a 1-D signal vs. time. In part, the disclosure generalizes peak-to-peak voltage (the most common way to assess amplitude in clinical EP) through using E field or equivalently voltage loops. Further, in one embodiment, it is desirable to maximize the magnitude of the vector $E(t_j)-E(t_i)$ as part of determining one or more OT metrics.

In light of the foregoing, a family of OT metrics, which can include various diagnostic vectors, can be defined that enhance data analysis and user interface display option by providing additional directional information. To achieve this, a vector m-hat or m̂ can be defined as a unit vector or a non-unit vector. In one embodiment, the unit direction vector m-hat from the loop signal is generated using the following relationship:

$$\hat{m} = \frac{E(t_j) - E(t_i)}{|E(t_j) - E(t_i)|}$$

and where $t_i$ and $t_j$ have been chosen to maximize $|E(t_j)-E(t_i)|$ and $t_j>t_i$ wherein bold denotes a vector quantity.

As shown in FIG. 3, m-hat is oriented in the direction of maximum (a relative extremum) peak-peak voltage. $E_m(t)$ is the signal E(t) projected onto m̂ (Em(t)=E(t)·m̂). This can also be written as $E_m(t)=<\hat{m},E(t)>$, where the inner or dot product of two vectors quantities a and b is <a, b>. In one embodiment, $E_m(t)$ is another example diagnostic vector.

As defined above by the order of $t_i$ and $t_j$ the vector m̂ has a defined direction. This direction however is arbitrary, ambiguous to ±180°. Unit direction vector a-hat represents a best estimate of activation direction based on phi-dot and Ea. M-hat provides information about the axis of propagation distinct from activation direction â and potentially more reflective of tissue properties. M-hat is independent of physical electrode orientation.

In one embodiment, other OT metrics in addition to m-hat can be generated. As noted above, it is possible to generate Em(t) by projecting the E-field onto m-hat. Vm(t) may then be found by Vm(t)=Em(t)*Electrode Spacing. This scalar voltage signal is proportional to Em(t) but in more familiar units (mV). Both of these signals are independent of catheter orientation. Vm(t) contains the largest peak-peak voltage for a depolarization (referenced to interelectrode spacing), in cardiac or other tissue which can be used to determine meaningful and robust characterization of local tissue properties.

Figure 5:
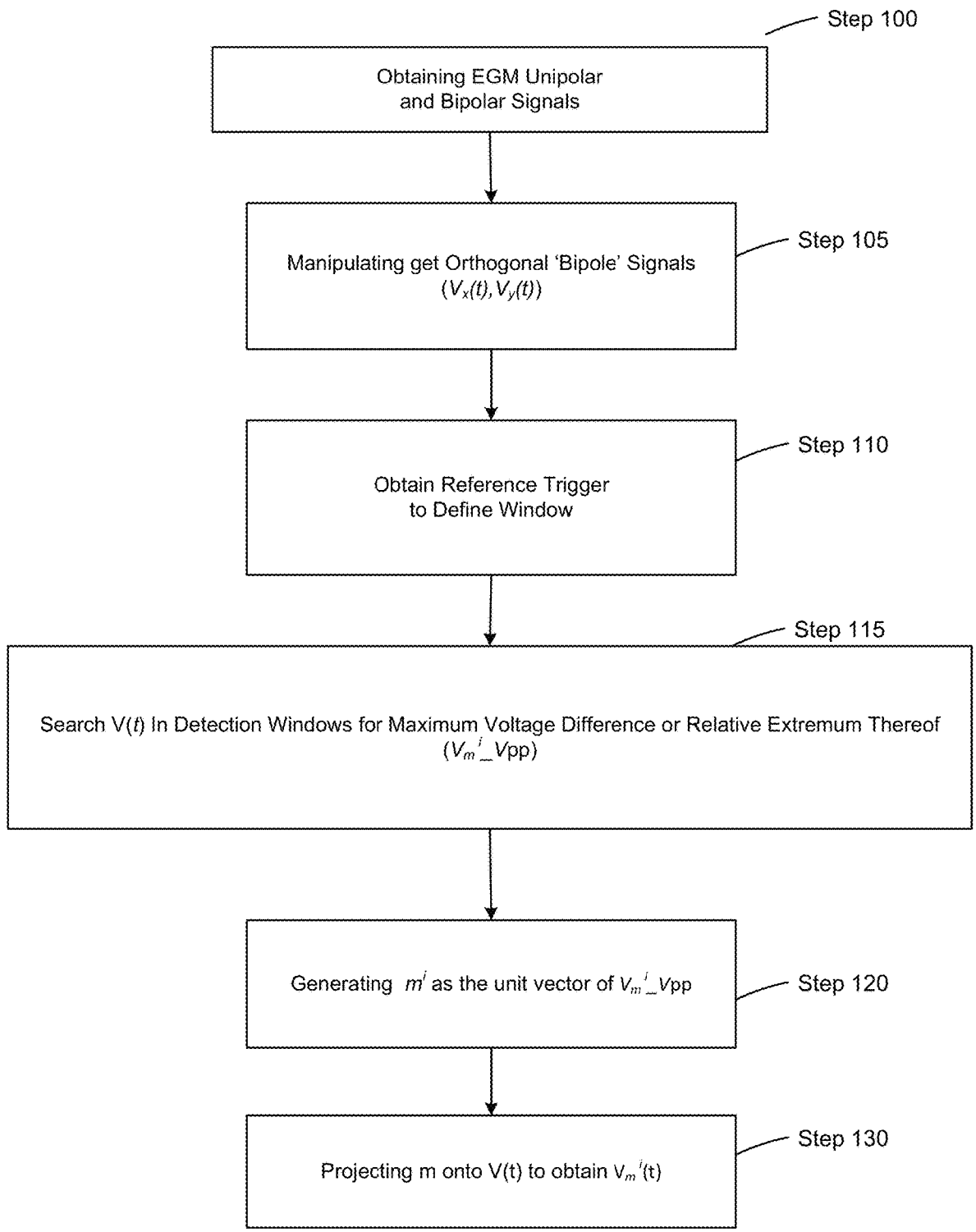
FIG. 5 is a flow chart showing a method to generate m-hat and a related OT metric Vm(t) using a reference trigger or reference signal.
Figure 7A:
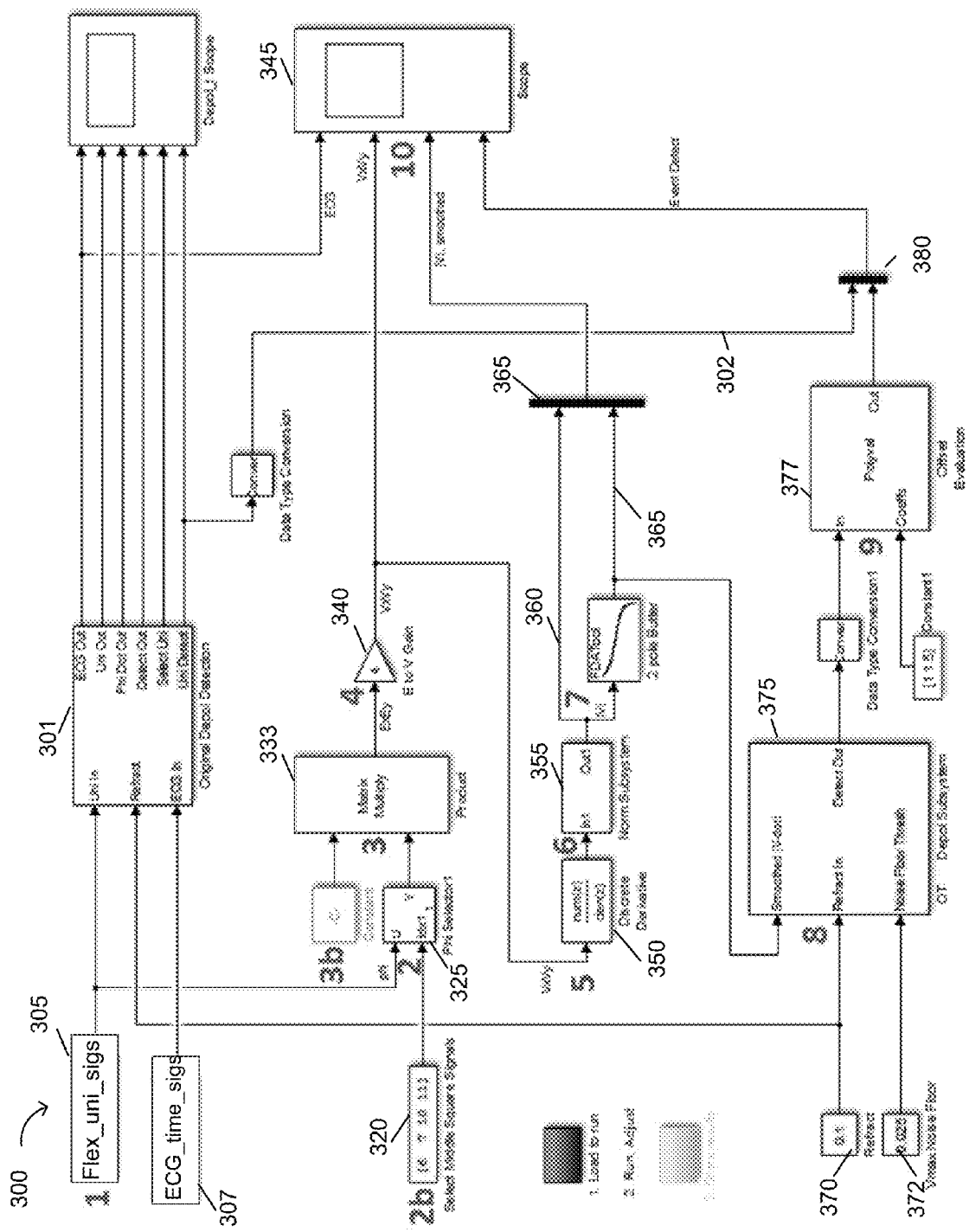
FIG. 7A is a block diagram of a system suitable for generating a reference trigger or reference signal.

A general method to generate m-hat using a reference signal as generated using the system of FIG. 7A is shown in FIG. 5. In one embodiment, the method includes obtaining EGM unipolar and bipolar signals (Step 100). Given these signals, which are typically stored in one or more electronic memory devices, processing of the signals occurs. In one embodiment, processing the unipolar and bipolar signals is performed to obtain the vector V(t) from its orthogonal components ($V_x(t), V_y(t)$) along the catheter's x axis and y axis (Step 105). A reference trigger can be determined generally or using one of the specific approaches described herein (Step 110). The reference trigger is used to define a window for searching for voltage values.

Accordingly, the method may include searching V(t) over a defined window for the maximum voltage difference or relative extremum thereof, which is identified as Vm_Vpp. (Step 115) After the search to determine Vm_Vpp, the axis of this maximal span is generated as the unit vector m or m-hat. (Step 120). Further, once the unit vector m has been generated, V(t) can be projected onto m to obtain the maximal bipole signal Vm(t) (Step 130).

The perpendicular direction to vector m-hat, m-hat-perp, can also be generated by vector operations. m-hat-perp, in turn, as another OT metric can be used to determine smaller peak-peak voltages that may be meaningful in defining late potentials or fractionation, by attenuating large dominant direction signals or other properties. Contrasting voltage measurements obtained by projecting E(t) or V(t) onto m-hat and m-hat-perp can provide information about local tissue properties. Em_perp(t) and Vm_perp(t) can be generated from m-hat-perp, and used to assess data sets to detect or evaluate conduction, complexity, and arrhythmogenicity related signals. The foregoing vectors are examples of diagnostic vectors suitable for operating upon various other vectors and functions.

M-hat is unique from activation direction a-hat, and together their agreement can serve as a quality measure. Discrepancies between the two may be indicative of pathology that can initiate or sustain an arrhythmia. This feature is shown in FIG. 4 by the angular deviation measure S.

Figure 4:
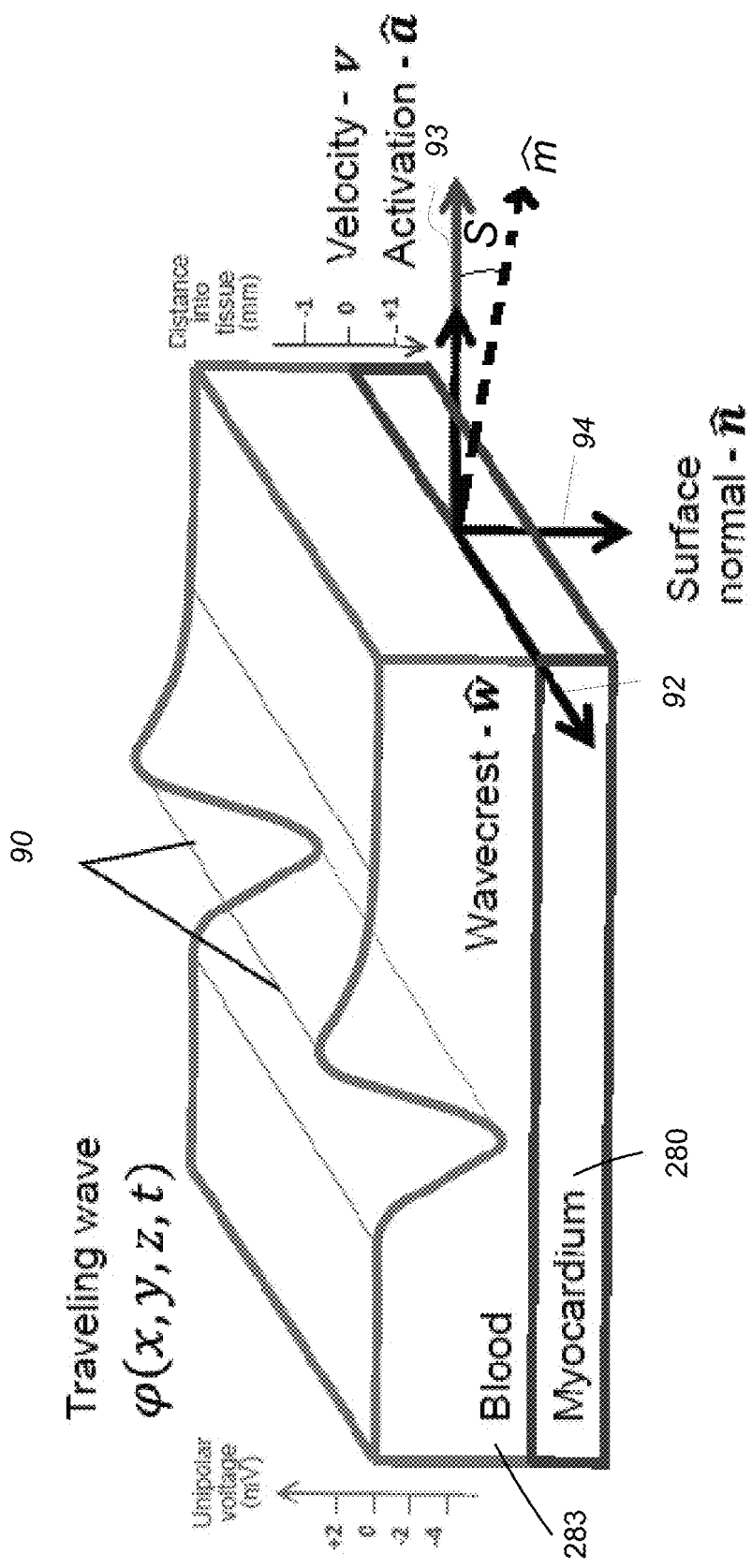
FIG. 4 is an illustration showing the activation, wave crest, surface normal, and conduction velocity directions for a traveling wave relative to a vector m-hat and an angular deviation relative to a-hat.

FIG. 4 illustrates the unit activation direction vector 91, wavecrest vector 92, surface normal vector 94, wavefront crest 90, and conduction velocity vector 93. M-hat is typically aligned with the unit activation vector 91. To the extent it deviates from activation 91 by an angle deviation S, the amount of deviation of S can serve as a threshold for diagnostic purposes. A single depolarization wavefront 90 is depicted based on a unipolar traveling wave voltage signal, φ(x,y,z,t). Propagation of the depolarization wavefront 90 occurs from left to right in the view. The catheter orientation independent omnipole signals En and Ea possess characteristic shapes and amplitudes in normal myocardium.

In addition to angular deviations and directional trends, m-hat can be used to generate other OT (signals and) metrics. In turn, such metrics can be used for subsequent data analysis. For example, the inherent separation of Em_perp(t) from E(t) as a non-dominant signal allows signals from fibrosed and irregular conduction pathways to be discernable relative to healthier tissue signals. As a result, abnormal early or late potentials may be more clearly visualized. Accordingly, by including Em(t) and Em_perp(t) as OT metrics in conjunction with the others described herein it may be possible to more accurately recognize true far field signals.

In the absence of a navigational system (such as NavX), the above metrics may be obtained and visualized in an EP recording system from ideal electrode positions to acquire results similar to the 3D full (NavX coordinate) calculation. Typically, the results will be more robust to NavX distortions.

Where navigational and/or 3D mapping systems are available, the OT metrics (including m-hat, m-hat-perp) can benefit by being portrayed with respect to the cardiac anatomy. M-hat and m-hat-perp can be transformed from an ideal catheter coordinate system to a 3D navigational coordinate system where additional value is derived from anatomic context such as can be seen for example in FIG. 16 (discussed in more detail below).

In the 2D case, it is straightforward to obtain a second unit direction vector m-hat⊥ (also ambiguous to ±180°) which is perpendicular to m-hat. In the 3D case, both m-hat and a vector normal to the plane of the clique's electrodes, n-hat, are operated upon to derive m-hat⊥. The scalar E or V EGM signals perpendicular to m-hat can be determined using a unit vector and the appropriate reference electrode spacing. The unit vector is m-hat⊥, $\hat{m}_\perp$.

$$E_{m\perp}(t) = <\hat{m}_\perp, E(t)> \text{ and } V_{m\perp}(t) = E_{m\perp}(t) \cdot \text{Reference Spacing,}$$

wherein the Reference Spacing refers to the center-to-center inter-electrode distance (e.g., 4 mm for the Advisor™ HD Grid Mapping Catheter). $E_{max\perp}$ and Vmax⊥ are peak-peak values of Em⊥(t) and Vm⊥(t). These signals may be more sensitive and specific for fractionation and LAVA/late potentials which are ablation targets because the larger signals occur along a perpendicular direction.

Differences between m-hat and a-hat directions (0-90° since polarity of m-hat is arbitrary) have been observed in certain disorganized propagation conditions. As mentioned above, they tend to be closely aligned for propagation in homogeneous tissue. Accordingly, a discrepancy between them may be indicative of pathology that can initiate or sustain an arrhythmia. One implementation is to make this assessment at a particular location for just a single beat and a single clique of adjacent electrodes.

A more reliable assessment for that location could result from observations over time (a few successive beats). A mean or median angular discrepancy of say >15° might indicate underlying EP complexity and arrhythmogenicity, while <10° indicates a regular simple rhythm (SR, Flutter, etc).

In terms of detecting or correlating catheter-measured EP data with an event, a state of a subject under test, or another parameter various metrics can be considered such as angle deviations, loop eccentricities and others. In one embodiment, such a method includes determining one or more directional deviations between m̂ and â. In turn, it is then possible to generate an alert when the one or more directional deviations exceed a threshold. An alert gives an end user notice and permits enhance diagnostic review and additional testing.

In one embodiment, the threshold used to evaluate angular deviations S (see FIG. 4) relative to m̂ and â is based on the variations in healthy tissue when catheters are held in the same spot. Based on experiments and trials, 95% of angular deviations between a-hat and m-hat in this condition lie within a range of about 15 degrees or less. In one embodiment deviations of angular distances S that range from about 15 degrees to about 20 degrees or more can be used to set a threshold for abnormal tissue characteristics and potentially indicative of arrhythmogenic tissue.

In one embodiment, S values that range from about 15 degrees to about 20 degrees or S values greater than about 15 degrees can be used as a threshold to perform tissue ablation, perform further diagnostic analysis to assess procedure selection, or generate an on-screen alert for the end user to give them notice of the relevant threshold being met or exceeded. Further reliability of one or more measurements or outputs to an end user can also be increased within a single beat by making angular discrepancy observations over nearby or all catheter cliques, using a similar threshold for complexity and arrhythmogenicity.

Figure 6:
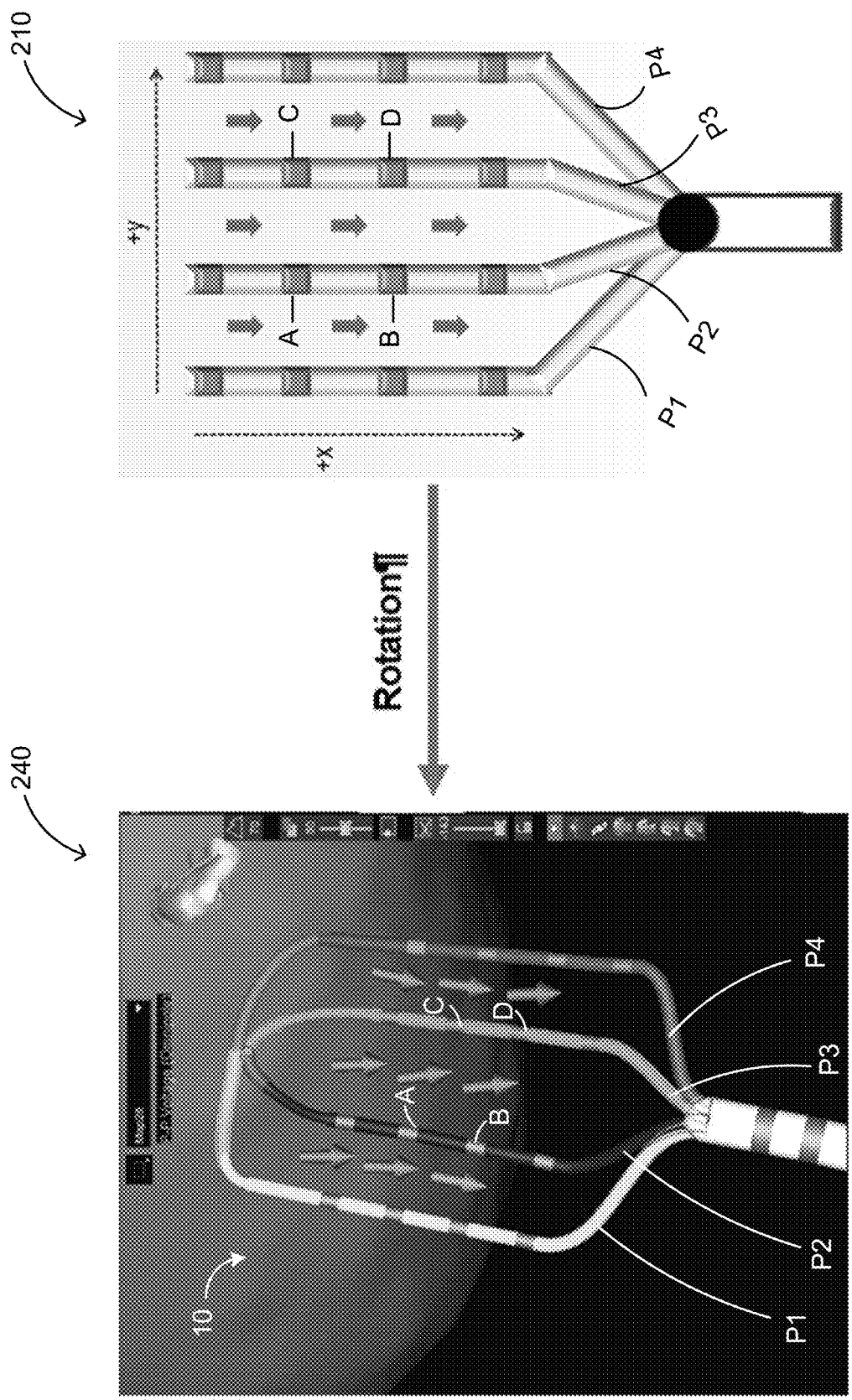
FIG. 6 is a schematic illustrating electrode location and representations of m-hat in the context of both catheter and 3D body coordinate frames (involving rotation and translation).

FIG. 6 is a schematic illustrating electrode location and representations of m-hat in the context of coordinate system changes of a diagnostic catheter. An HD Grid catheter displayed in SJM's EnSite Precision™ cardiac mapping system is shown on the left. The central square clique having electrode vertices ABCD is shown on the catheters which have splines P1-P4. Six downward pointing arrows are shown in a 3 by 3 arrangement. These arrows represent the m-hat vector direction, or the 3D direction of maximal bipoles in the context of patient anatomy. On the right side of the FIG. 6, an idealized 2D representation of a catheter, also with six arrows representing the m-hat direction, is shown. This catheter coordinate frame (x and y axes, or x,y,z axes) does not require navigation-derived electrode coordinates. As a result, these catheters may function independent of NavX or with severe distortion. The catheter coordinate frame facilitates calculation of one or more of the OT metrics. It may then be transformed to the patient's anatomical coordinate frame using rigid body rotation and translation derived from the positions and orientations of the catheter's electrodes in both coordinate frames.

FIG. 7A is a block diagram of a signal generating system 30 suitable for generating a reference trigger signal. In one embodiment, the disclosure includes a bipole-based but catheter orientation independent (OT) reference/trigger signal. The combined advantages of bipole rejection of far field signals and catheter orientation independence improves reference signal accuracy. In one embodiment, the reference trigger generation uses all possible clique bipoles to obtain in the 2D case $E(t)=(E_x, E_y)(t)$. From this functional relationship using such a collection of bipoles, a single signal that reflects the energy in all component bipoles is generated. Although bipoles are used, the calculation remains directionally independent. As a result, reference triggers may be more consistently reliable than traditional methods.

Returning to FIG. 7A, the top right block of the diagram 301 depicts input ECG information and a legacy approach of reference signal generation that uses all measured electrograms from unipolar signal block 305 (without bipole involvement). All of the unipoles are routed by default from source 305 as part of a first step to selector block 325 shown as step 2. At step 2b, a selection of key bipole signals corresponding to the central clique (such as clique ABCD discussed above with regard to FIGS. 2A and 2B)) are identified. Unipole electrograms 6, 7, 10, and 11 identified in signal section block 320 and are selected at the selector 325 for transmission onward. All of the other signals from the source block 305 are blocked and do not pass the selector 325.

Next, at matrix multiplier 333, the unipole signals and their associated bipole signals are combined together with various weights to determine electric field components along the catheter x-axis and y-axis. The constant C in output block of step 3B specifies the weighted combinations. C may also contain the interelectrode spacing in an alternative embodiment. As shown, however, two signals Ex and Ey are output to converter 340 and subsequently converted into voltage signals $V_x$ and $V_y$.

In one embodiment, which is optional in some cases, the derivative of the $V_x$ and $V_y$ signals is obtained at derivative block 350. Next, the time derivatives of the $V_x$ and $V_y$ signals are transmitted to normalization block 355. Within this block, the signals are operated upon to normalize them to generate a Euclidean magnitude that incorporates the directionality of the bipoles and the original omnipoles. This output signal has the form of an omnidirectional energy signal. Next, normalization block 355 sends the omnidirectional signal to low pass filter block 363. Once filtered, the resultant signal then enters a threshold crossing and detection block (block 375). Finally, several intermediate signals from the processing as well as the output of block 375 are displayed on scope 345 for review by a user. This provides an overview of the main processing steps.

To provide some additional detail of some of the processing blocks it is useful to return to Block 375. After low pass filtering to smooth the energy signal, the first local maximum above the noise floor is detected for the filtered signal at depolarization subsystem 375. A conventional refractory period is then in effect which is used to exclude false multiple depolarizations as part of this subsystem 375. In addition, a noise floor and/or a threshold detector can be used to further shape and extract meaningful signal data. In one embodiment, the threshold detector is a zero-crossing detector. The offset evaluation block 377 provides further optional signal shaping before the reference signal is generated as an output from block 375 or 377 and displayed on scope 345. The dotted reference signal is shown as dotted trace in FIG. 8D.

In one embodiment, the reference signal is generated using a selected subset of representative bipoles. The reference signal can come from (for HD Grid or other electrode-based catheter) the middle square clique. Accordingly, its use can be extended and remains relevant to all surrounding cliques of any type. Alternatively it may come from a user selected clique that is used for all catheter cliques. Finally, it may come from each clique, making detection independent. This would be most useful for situations when the catheter is placed over a line of block where the depolarization times of clique signals from a single catheter could be substantially different.

Figure 7B:
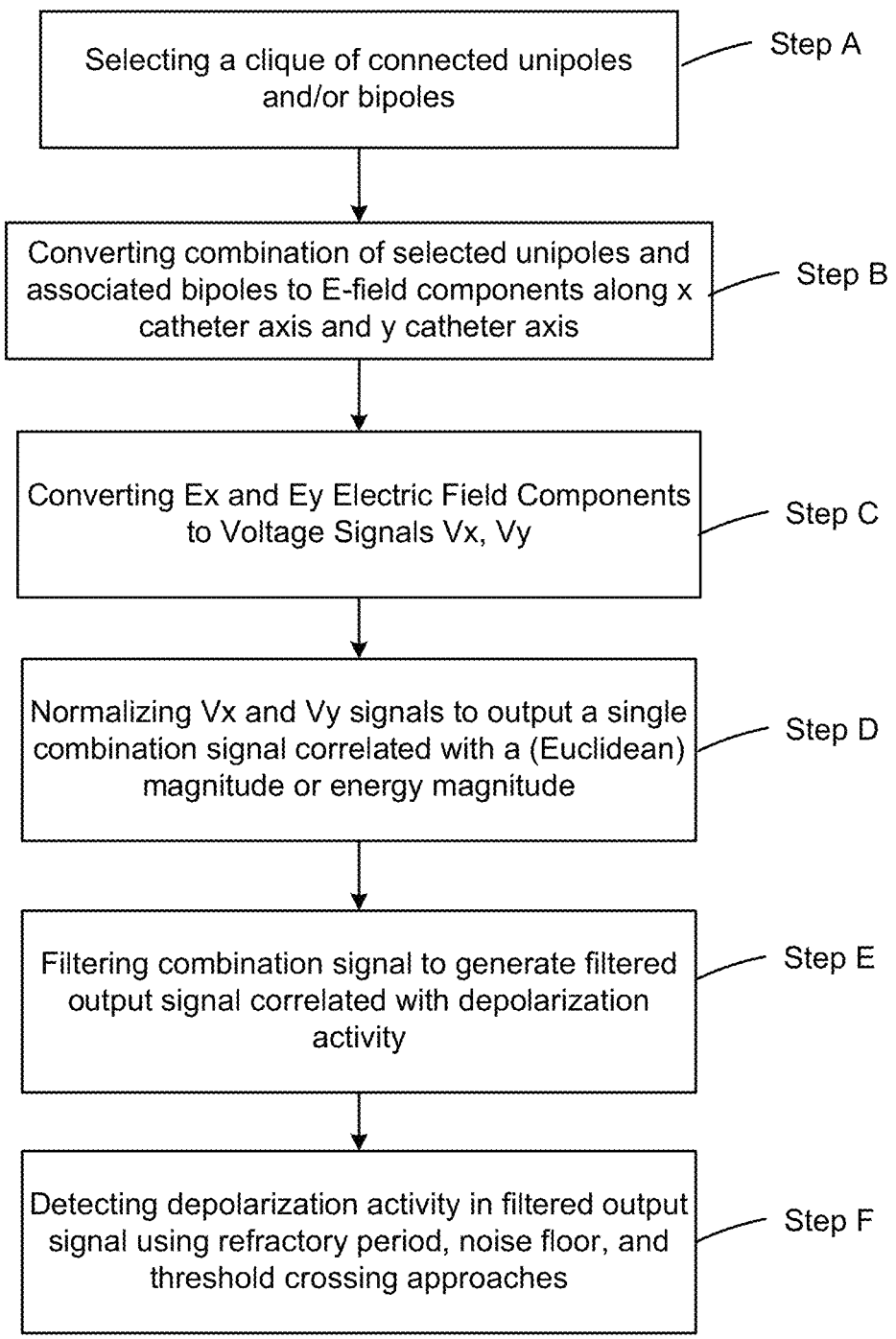
FIG. 7B is a flow chart showing a method to generate an orientation independent reference trigger or reference signal from a combination of unipole signals and bipole signals.

FIG. 7B shows an exemplary method for determining a direction independent reference trigger with the benefits of using bipoles and omnipoles. In part, the method includes selecting a clique of nearby electrodes in a non collinear arrangement (Step A). Converting combinations of selected unipoles and/or associated bipoles to E-field components along x catheter axis and y catheter axis is another step (Step B). The method can also include converting Ex and Ey electric field components to voltage signals $V_x$, $V_y$ (Step C). Normalizing $V_x$ and $V_y$ signals to output a combination energy signal correlated with a Euclidean magnitude or energy magnitude is another step (Step D). The method can also include filtering the combined energy signal to generate filtered output signal correlated with depolarization activity (Step E). The method can also include detecting depolarization activity in filtered output signals using refractory period, noise floor, and threshold crossing approaches (Step F).

Figure 8A:
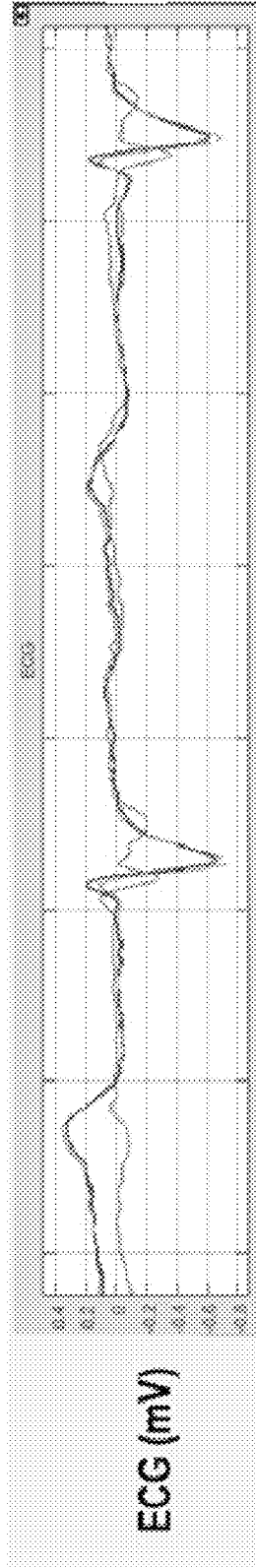
FIGS. 8A-8D show a series of plots generated using the signal processing system of FIG. 7A in which the dotted signals have been low pass filtered.
Figure 8B:
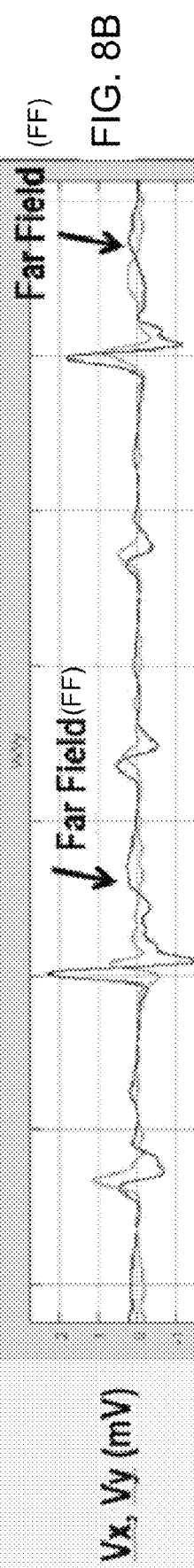
Figure 8C:
Figure 8D:
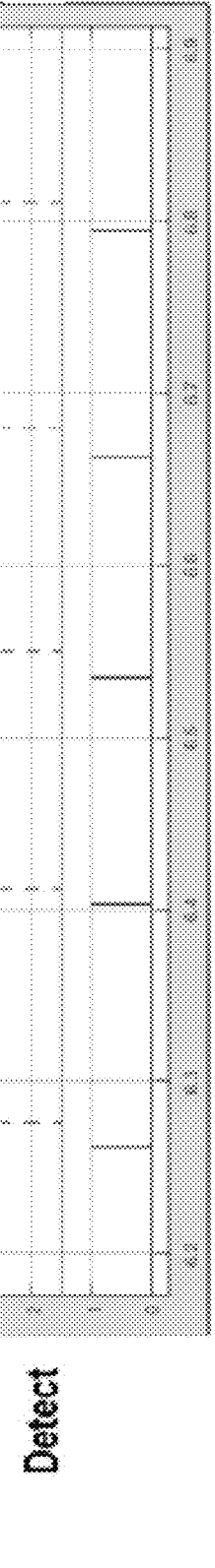

FIGS. 8A-8D show a series of plots generated using the signal processing system of FIG. 7A. FIG. 8A shows ECG traces synchronized in time to the signals below in the other plots. FIG. 8B shows the $V_x$, $V_y$ signals from FIG. 7A and the associated far field noise regions FF. FIG. 8C shows the signal generated from normalizing the $V_x$, $V_y$ signals. The low pass filtered signal from FIG. 7A is shown with the dotted lines. The reference signal uses four unipole signals to create six effective bipoles, naturally reducing common mode and far-field noise as discussed above. The method may be supported by a combination of moving average filters, derivatives, and lowpass filters as referenced in FIGS. 7A and 7B. In FIG. 8D, the dotted ticks or vertical spikes are generated using the steps of FIG. 7B or generated by the system of FIG. 7A. The dotted reference signals in FIG. 8D are slightly delayed from the EGM signals themselves as a result of the low pass filter's delay. Since this filter's group delay is known from its design, this can be compensated for to remove the delay.

Figure 9A:
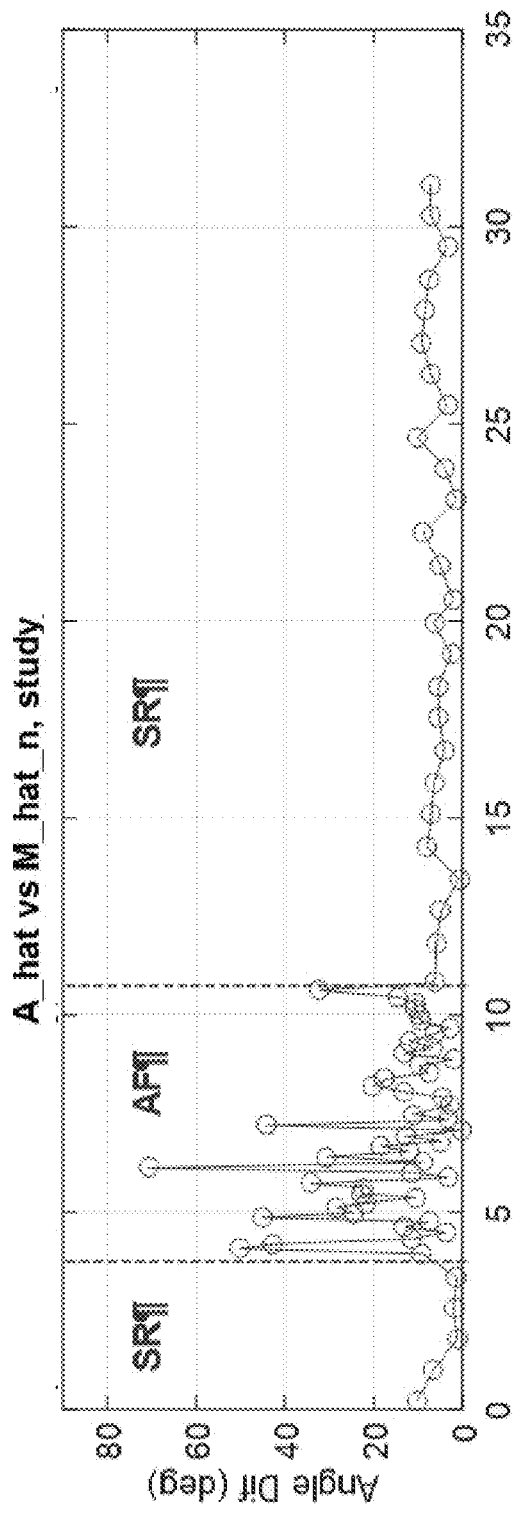
FIG. 9A is a plot showing angular difference S between the directions of activation (a-hat) and greatest peak-peak voltage (m-hat) adjacent a plot of respiration over time as shown in FIG. 9B.
Figure 9B:
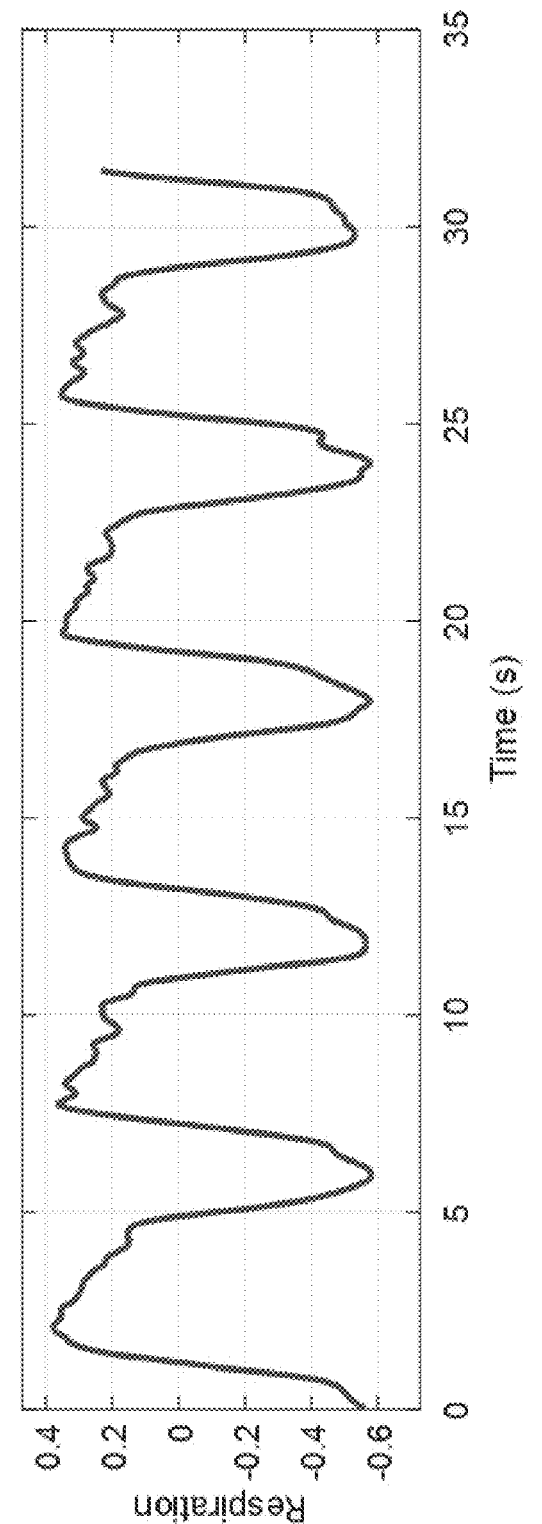

FIG. 9A shows angular difference between the directions of activation (a-hat) and greatest peak-peak voltage (m-hat), which correspond to S as shown in FIG. 4. The two vector directions diverge from times 4-11 seconds which correspond to AF beats. Times 0-4 and 4-32 seconds correspond to sinus rhythm, which is shown in FIG. 9B. In addition to considering angular deviations, S, the eccentricity of electric field loops can also be evaluated using m-hat and other OT metrics disclosed herein.

To provide context for the use of eccentricity, it is useful to consider another measure of eccentricity of the E-field or voltage loop by the ratio $E_{max\perp}/E_{max}$ which must always be ≤1. Very eccentric loops have a ratio <0.4 and reflect a predominance of healthy conduction in homogenous tissue. Round loops have ratios >0.6 and reflect complexity and possibly identify arrhythmogenic locations. In some embodiments, $E_{min}$ has been found to be proportional to or substantially the same as $E_{max\perp}$. Accordingly, $E_{min}$ may be used in lieu of or to otherwise replace references to $E_{max\perp}$ as described and depicted herein. $E_{min}$ and $E_{max}$ can also be described using the following relationships:

$$E_{min}=\min_\theta\{<[\cos\theta,\sin\theta],E_{loop}>\}$$

$$E_{max}=\max_\theta\{<[\cos\theta,\sin\theta],E_{loop}>\}$$

Eccentricity alone may be insufficient to characterize abnormal loop shapes. Loops may cross themselves or have significantly non-ellipsoid shapes. In these circumstances, the mismatch between loop area and circumference may be employed as an index of complexity, and Green's theorem may be applied to provide a polar-planimeter-related index.

Figure 10A:
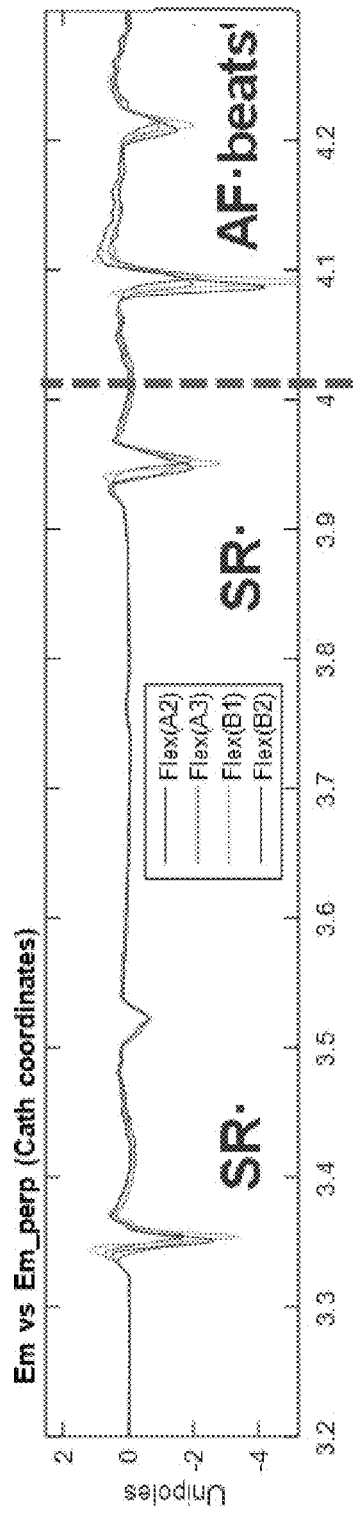
FIGS. 10A-10C are plots showing unipoles (FIG. 10A) Em (FIG. 10B), and $E_{m\perp}$ (FIG. 10C) from a study with sinus rhythm (SR) and atrial fibrillation (AF).
Figure 10B:
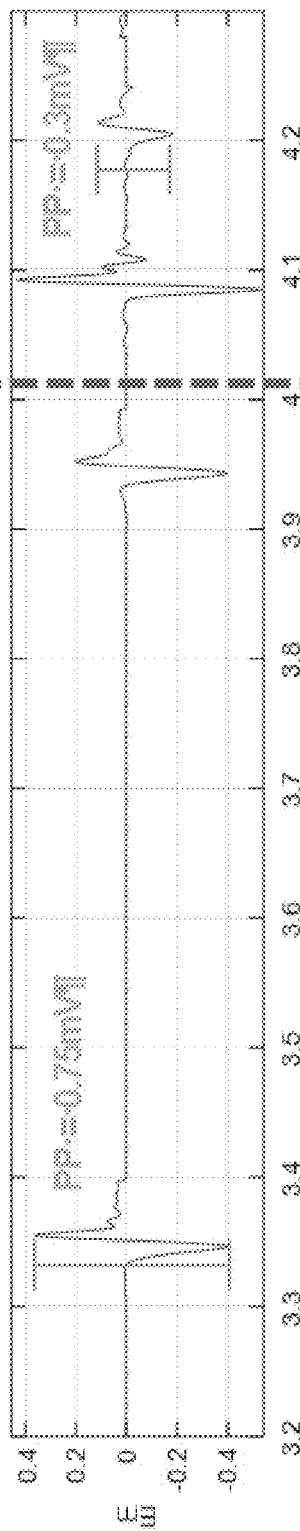
Figure 10C:
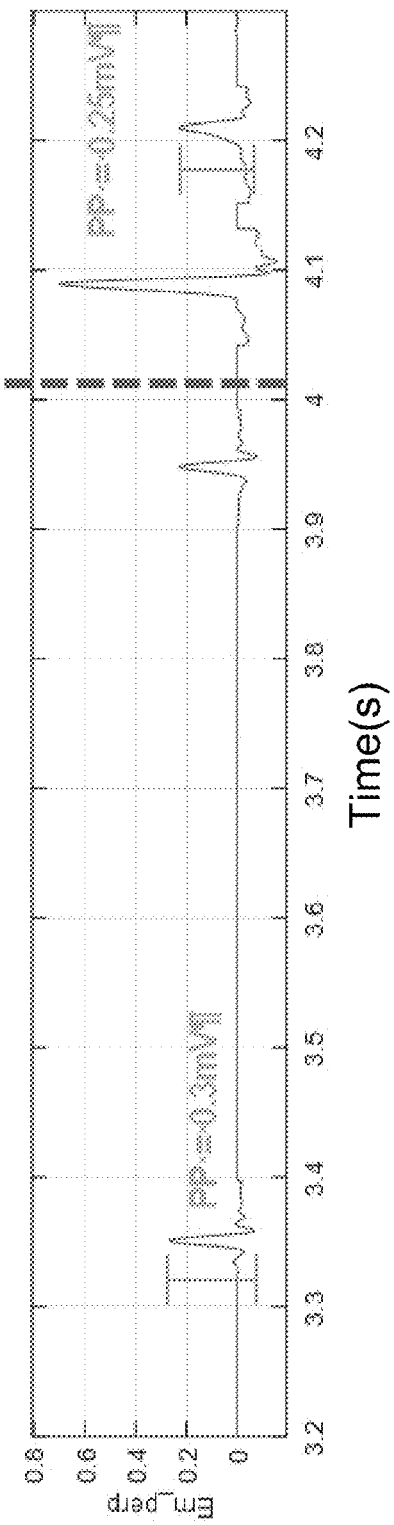

FIGS. 10A-10C are plots showing unipoles (FIG. 10A) Em (FIG. 10B), and $E_{m\perp}$ (FIG. 10C) from a study with sinus rhythm (SR) and atrial fibrillation (AF). The horizontal axis corresponds to time with units of seconds. The vertical axis values for the three figures correspond to unipole voltage (in mV), Em, and Em_perp, respectively as shown. These representations can be provided using electric field or voltage values. If using Em and Em_perp, then the vertical axis units are mV/mm. In turn, if using Vm and Vm_perp, then the vertical axis units are mV. For a given beat and square clique, the 4 unipole signals make $E_x$ and $E_y$ omnipoles from which an E(t) loop is created (see FIG. 3) and $E_m(t)$ and $E_m\perp(t)$ can be identified. The first two beats are SR, while the last two are AF. The ratio of Em_perp/Em is 0.4 for beat 1 and 0.83 for beat 4. This suggests that the E-field loop for beat 4 is nearly circular, or non-eccentric.

Another application of deriving two-dimensional electrogram characterizations at clique locations is that by separating dominant from nondominant (Em(t) and Vm(t) vs. Em⊥(t) and Vm⊥(t) respectively) signals, signals from fibrosed and irregular conduction pathways can be detected rather than the case where they are obscured by nearby healthier tissue signals.

Figure 10D:
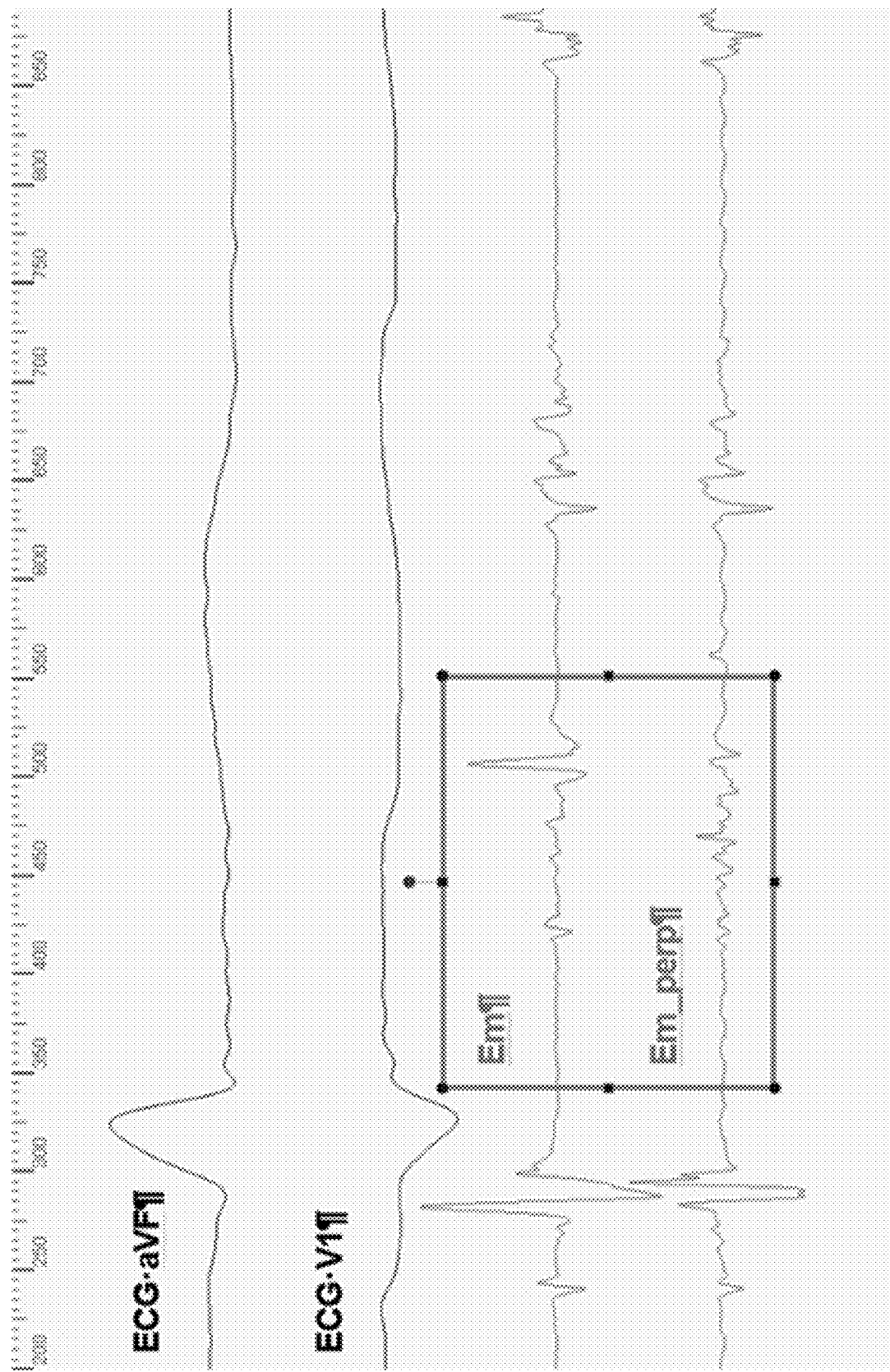
FIG. 10D is a plot of bipolar EGM signals from a sample AF beat resolved along the dominant (m-hat) and non-dominant (m-hat-perp) directions.

FIG. 10D is a plot of bipolar EGM signals from a sample AF beat resolved along the dominant (m-hat) and non-dominant (m-hat-perp) directions. As shown, the non-dominant signal contains a greater number of smaller sharp deflections, suggesting fractionation. Signals like this Em-perp may indicate complex conduction patterns, fibrosis, or fractionation suitable for ablation targeting.

M-hat derived metrics may be used to classify near-field and far-field signals that do not rely entirely on basis of frequency (far-fields tend to be low frequency) or timing (one type of far field is coincident with QRS) but rather on level of orientation dependence. If small in all directions (e.g. a small 2- or 3-D loop) EGM signal components are truly far field and one may safely ignore them, particularly for unipole derived signals or characteristics (e.g. phi-dot or unipolar $V_{PP}$). Upon identifying a unipolar signal that has little significant bipolar amplitude in any direction, it is useful to briefly blank or block the visualization and use of any of its derived signals and characteristics.

A similar approach may be used for the traveling wave treatment of OT. OT's separation of dominant (activation) from nondominant (wavecrest) signals (Ea(t) and Va(t) vs. Ew(t) and Vw(t) respectively) signals can help identify difficult to discern signals. As an example, this would include signals from fibrosed and irregular conduction pathways. A similar method can be used to help these signals standout from nearby healthier tissue signals.

User Interface (UI) Features and Exemplary Embodiments

The various m-hat and associate family of diagnostic vectors, and correlated parameters and operators, which apply generally to the OT and OIS embodiments disclosed herein can be used to generate display element and user interfaces. Such user interfaces and display elements can include maximal and minimal voltage values, maximal bipole signals, the directions of maximal bipoles, and color map displays (generally referred to as OT metrics or parameters in on embodiment). All of these and other vector and scalar data and signal can be displayed in various forms as graphical user interface elements. These can include scalar values, plots, and other indicia or other viewable or user selectable elements. In one embodiment, they are displayed in a 3D mapping system such as EnSite Velocity, which is commercially available from St. Jude Medical.

Generating a mapping with regard to color or other indicia such as hatching, shading, topographic representations, or symbols can be achieved by assigning a scalar value to a point in 3D space that corresponds to an electrode clique's centroid or the closest point on the nearby cardiac surface. For example, a colored dot or triangle in 3D space or as a color mapped region on a cardiac surface can be displayed to an end user. These symbols correspond to the clique centroid's 3D position.

In addition, m-hat information such as m-hat directions can be visualized or displayed to an end user to help interpret and improve user perspective relative to a catheter coordinate frame. Similarly, display of indicia such as arrows, line segments, cylinders of other information based on or correlated with m-hat can be used to improve catheter navigation. These indicia can make it easier to interpret geometry or maps in 3D NavX body coordinates. In one embodiment, these indicia or user interface components are represented in a 2D or 3D space as arrows or simply line segments since, as mentioned above, the maximal directions are ambiguous to ±180°. As shown in the user interface figures, the indicia or user interface components can be shown relative to the catheter and/or relative to a generated GSM or other information being displayed to an end user. All of these various embodiments can be displayed or used with a guide interface that is a representation of electrode grid and associated splines of a diagnostic catheter.

Various user interface components in the form of overlays, moveable screen elements, panels, color maps, and plots alone or in combination can be presented to the end user. Typically, the user interface components can be selected or toggled using commands or by user selection with an interface device on the applicable user interface and settings menu. In one embodiment, various user interface components can moved around on the display screen, rotated, and docked at default or user specified positions relative to other information displayed to the user. These features can apply to the guide user interface and electric loop interface discussed below with regard to FIG. 15.

Figure 11A:
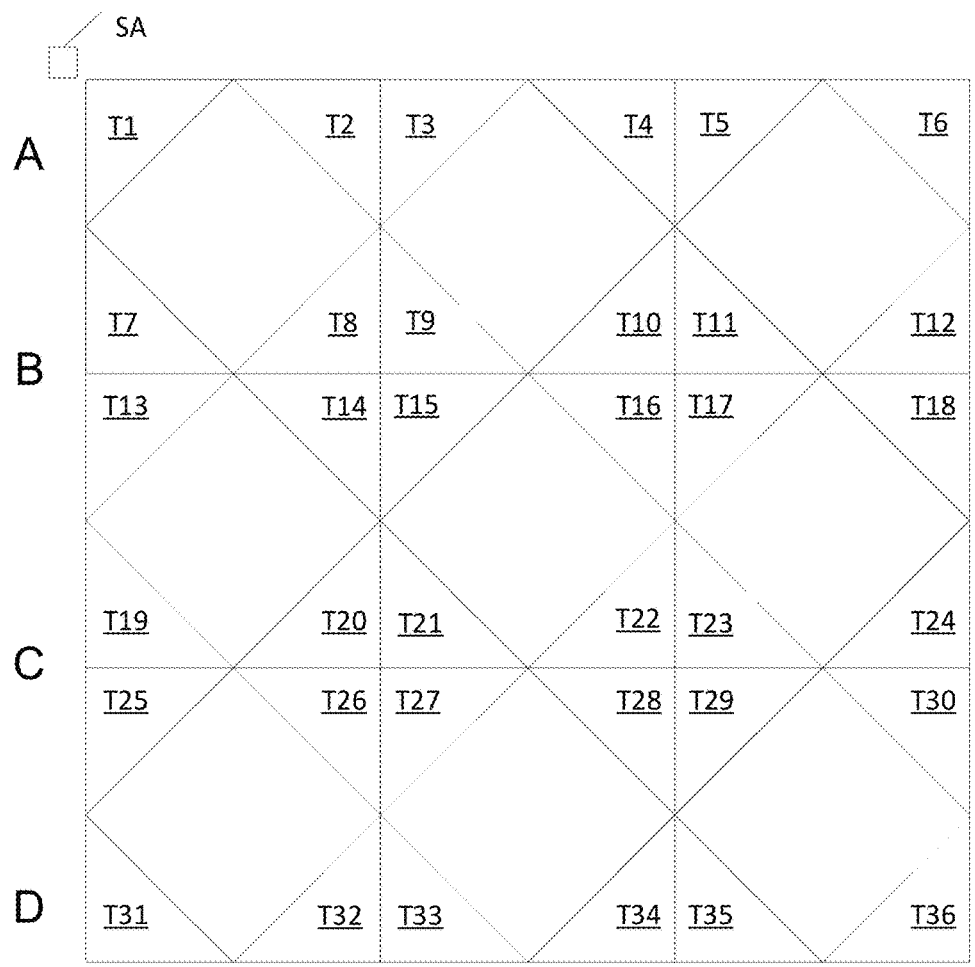
FIG. 11A is a user interface component that includes a guide user interface having a grid array of thirty-six user selectable triangular cliques suitable for triggering waveform display in response to each clique selected.

FIG. 11A is a user interface component that includes a guide user interface having a grid array of thirty-six user selectable triangular cliques suitable for triggering a waveform signal display in response to each clique selected. Any number of triangular cliques (1-36) can be selected with each triangular clique labeled T1 through T36. In some embodiments, signal values and scalar and m-hat values can be shown relative to these selectable user interface elements such as by an overlay on top of the triangular regions.

Figure 11B:
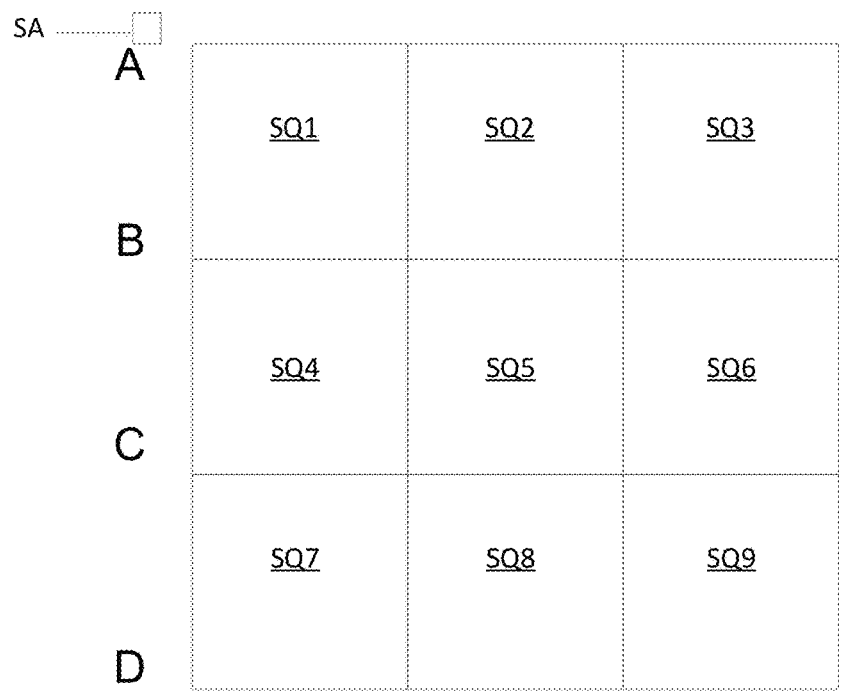
FIG. 11B is a user interface component that includes a guide user interface having a grid array of nine user selectable square cliques suitable for triggering waveform display in response to each clique selected.

FIG. 11B is a user interface component that includes a guide user interface having a grid array of nine user selectable square cliques suitable for triggering waveform signal display in response to each clique selected. Any number of square cliques can be selected (1-9) with each square clique labeled SQ1 through SQ9. In some embodiments, signal values and scalar and m-hat values can be shown relative to these selectable user interface elements such as by an overlay on top of the square regions. These overlays can include bipole values and other data. A select all (SA) interface is shown in the top left side of FIGS. 11 and 11B. The SA interface allows for selection or un-selection of all cliques. The guide interfaces are typically color matched to another legend or other displayed data such as color coded splines or corresponding signals.

FIGS. 12A-12F are user interface components that includes a guide user interface and waveforms displayed in response to the user selection of various combinations of square and triangular cliques. With regard to FIGS. 12 A and 12B, user interface elements in the form of guide user interfaces 400 and 405 are shown. Each user interface includes selectable graphical elements for triangular cliques (FIG. 12A) and square cliques (FIG. 12B). The selection of a single omnipolar clique for both triangular (FIG. 12A) and square (FIG. 12B) cliques is depicted here. Triangular clique T21 and central square clique SQ5 have both been selected by the user or in response to a programming command or script. A select all user interface toggle or button SA is shown, when selected all cliques are selected and deselected respectively as shown, for example, in FIGS. 12E and 12F.

A representation of a diagnostic catheter 407 in which the splines A, B, C, and D join in the catheter's shaft are seen oriented relative to the left column having the same labeling. Thus, elements of the A row can be colored coded using the color yellow (Y), as shown by the one exemplary cell that is labeled. An exemplary element of the other rows is also color coded using red (R), green (G), and blue (B). In some embodiments, all of the elements of a row are color coded or otherwise coded with suitable indicia. Each interface provides a grid layout that is mappable to the grid of a given diagnostic catheter and its splines (rows). For each selected clique, such as for example triangular clique T21 or central square clique SQ5, the maximal bipolar electrogram signal is shown (called omni trace here). The reference signal generated using the system of FIG. 7 or otherwise is also shown as is the ECG trace. When all cliques are selected 36 and 9 traces are displayed as shown in FIGS. 12E and 12F.

The triangle cliques are labeled T1-T36 as was shown in FIG. 11A. The square cliques are labeled SQ1-SQ9 as was shown in FIG. 11B. Regions 420, 425 on the left side of each figure and 422, 427 on the right side are bands or curtains that bound the central data region of interest for all of the signals shown.

Figure 12C:
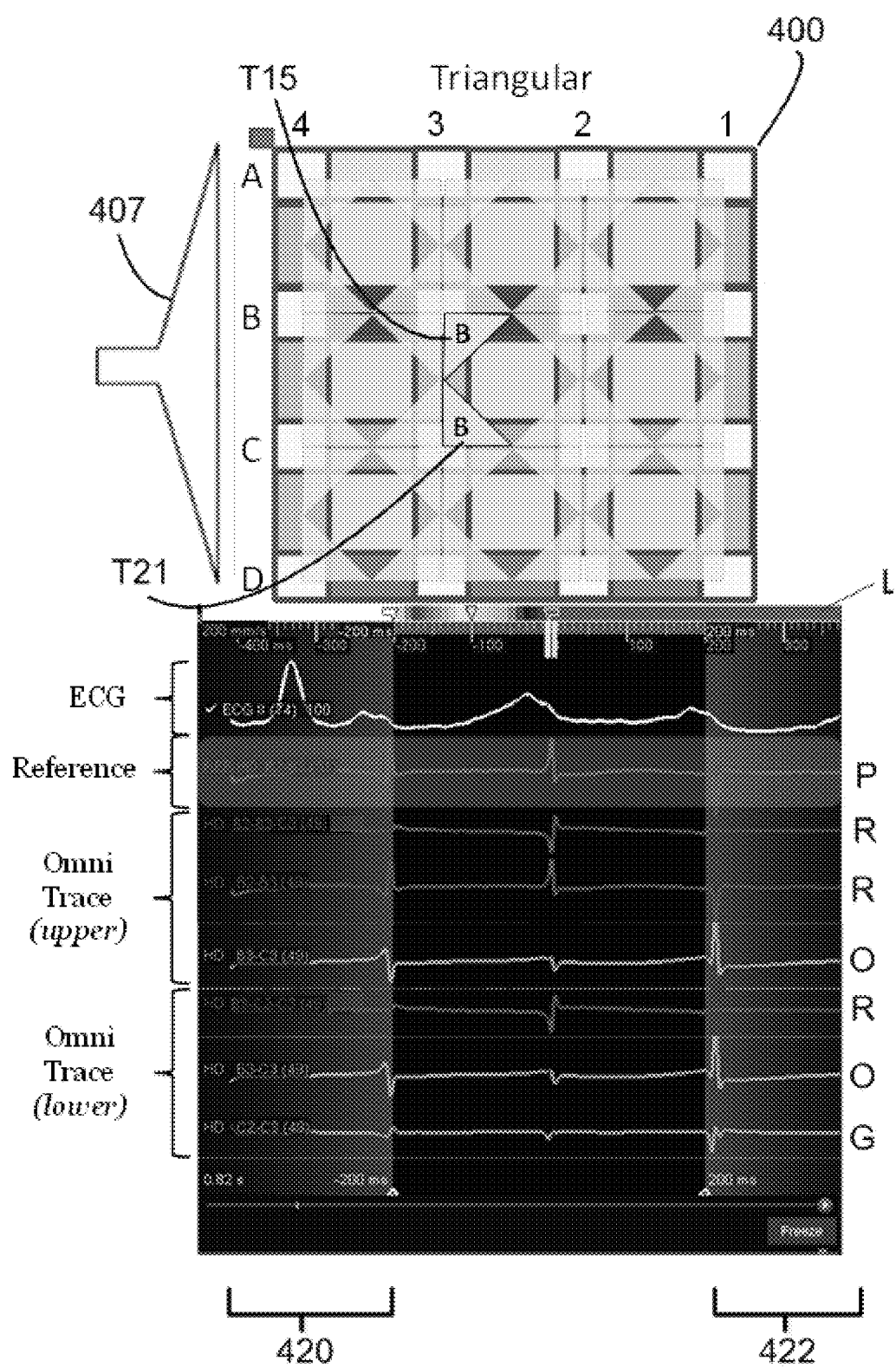
Figure 12D:
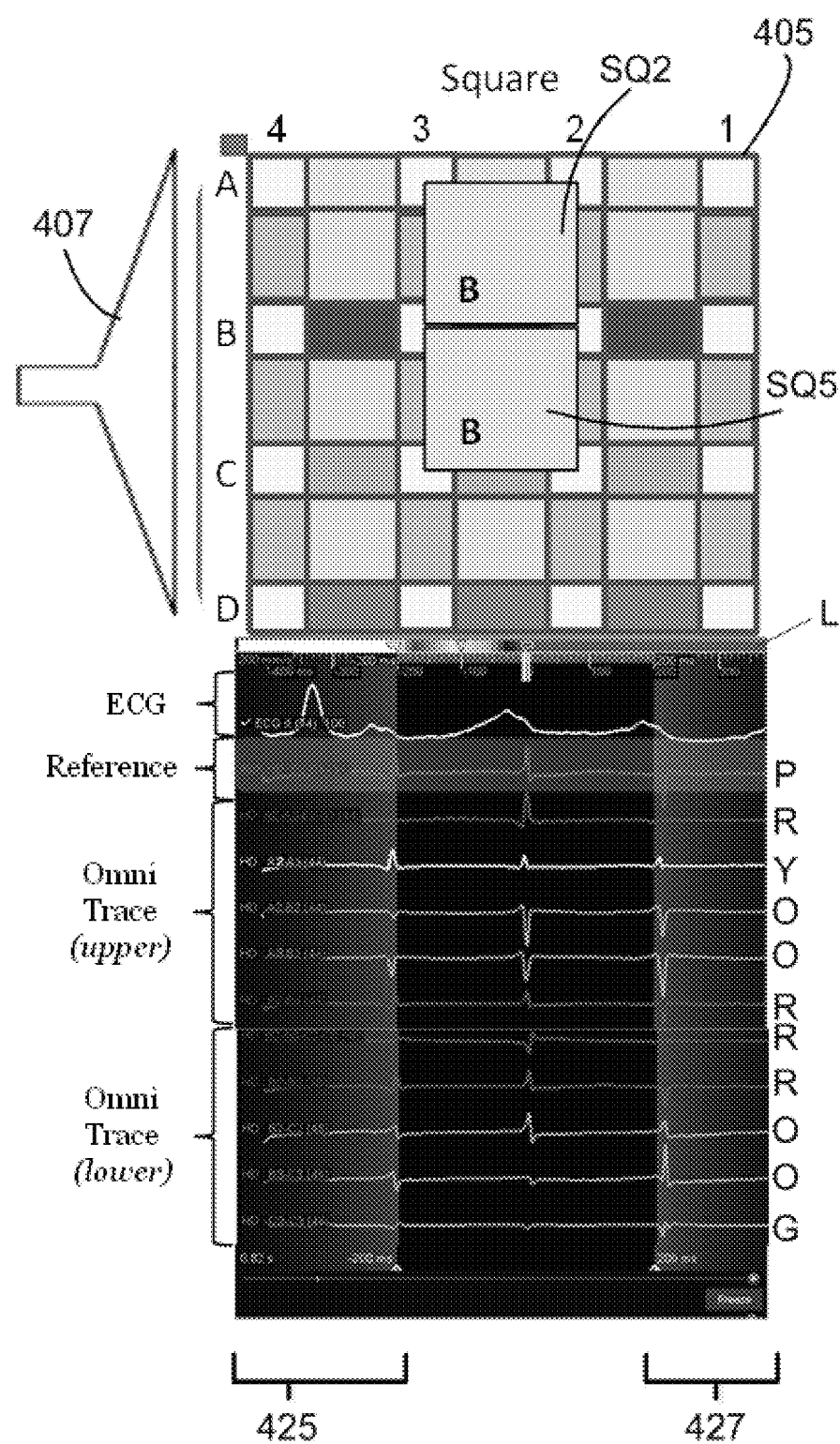
Figures 12E, 12F:
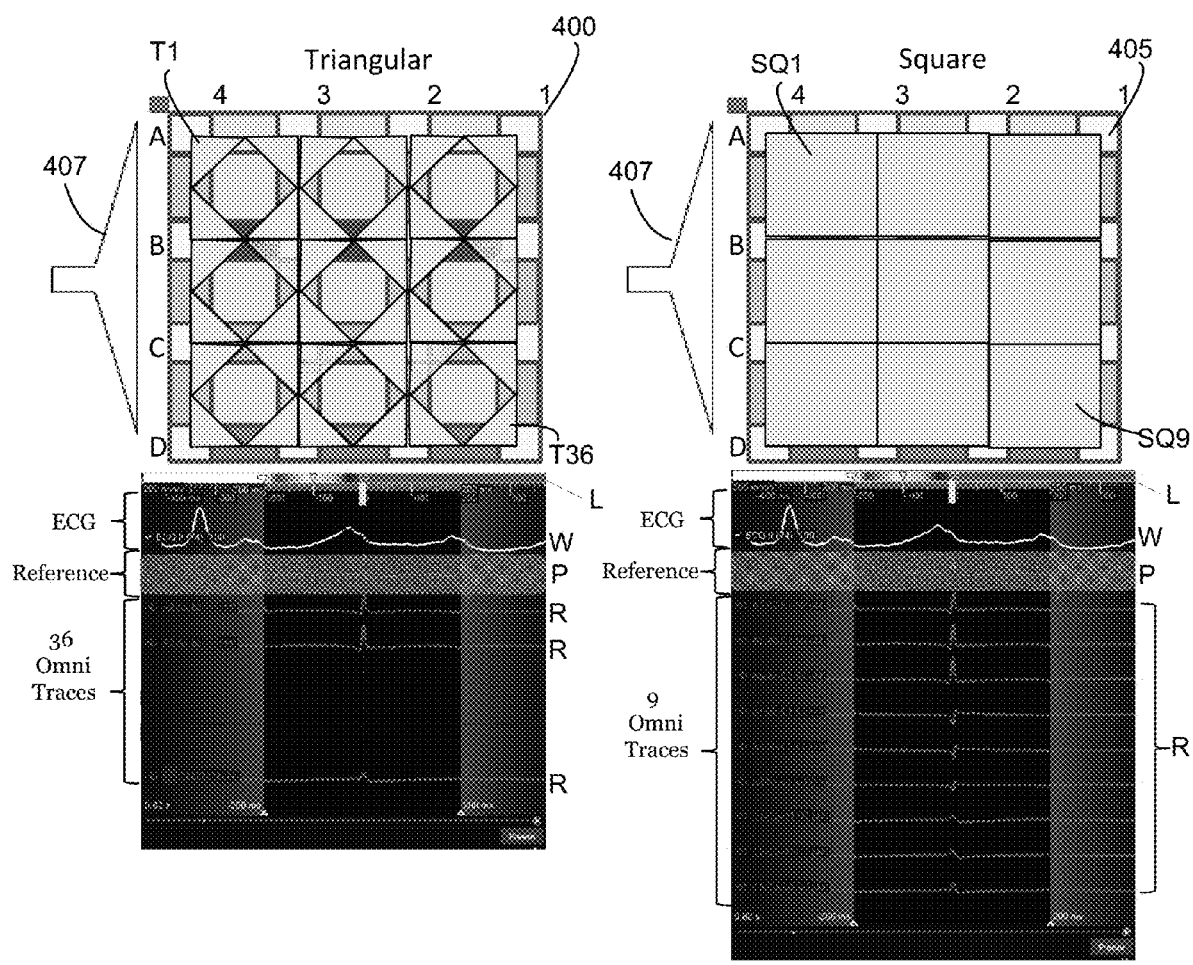

In FIGS. 12C and 12D, two omnipolar cliques for both triangular and square cliques are depicted. Triangular clique T21 and central square clique SQ5 have both been selected by the user or in response to a programming command or script. In addition, triangular clique T15 and square clique SQ2 also have both been selected. The solid triangular object having a B on T15, T21, SQ5, and SQ2 indicates its constituent bipoles are to be shown (in addition to the omnipole trace) on the guide interface. For each selected clique (solid triangular object) the maximal bipolar electrogram signal is shown (called omni trace here). Trace colors correspond to what is shown in the guide. In one embodiment, the solid triangular object is color coded. In the example shown, the object is yellow. The traces in FIGS. 12A-12B are color coded using P for purple, R for red, O for orange and G for green as shown on the right side of the various traces. Other indicia can be used to identify such objects in the interface.

T15 for example spans red and orange spline portions in interface 400. T21 for example spans green and orange spline portions in interface 400. Accordingly, in general, color maps of spline portions and omnipole, bipole, and unipole signals can be matched in various embodiments. In addition, whenever color or color maps are referenced, other mapping or tracking indicia can be used. Exemplary orange splines are shown with an "O" corresponding to the orange color. In some embodiments, all of the splines are color coded or otherwise identified.

In FIGS. 12E and 12F, all cliques (36 triangles at left and 9 squares right) result in display of all omnipolar waveforms in the map acquisition window. The SA interface in the upper left corner of the guide is used to toggle between all and no selected cliques. In turn, trace colors (region below interfaces 400 and 405) correspond to the selected color for omnipole signals. In this interface layout, the color selected is red and also identified by "R" as shown. Other colors and indicia can be used in lieu of the color red without limitation.

Figure 13:
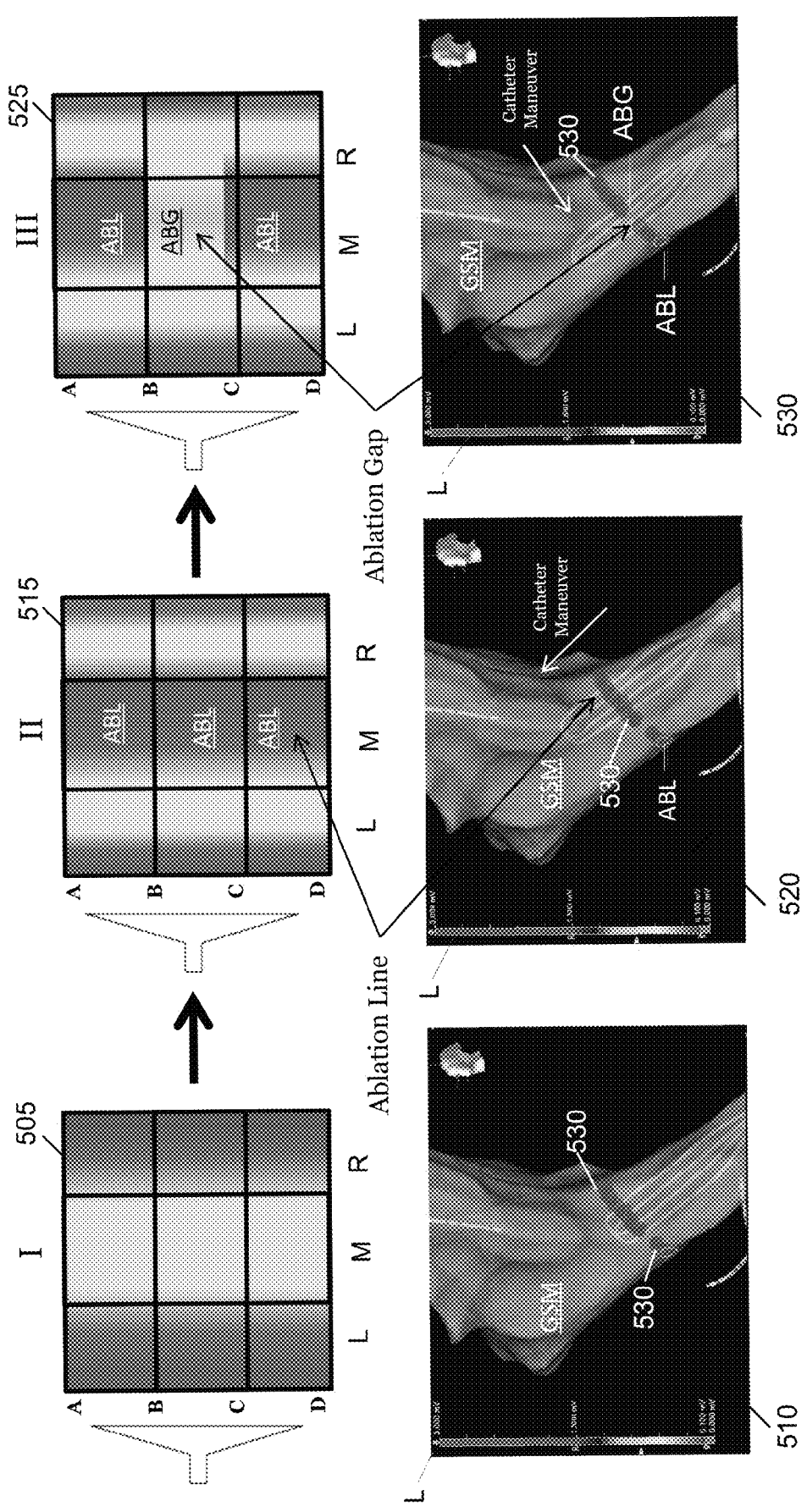
FIG. 13 is a user interface component that includes a color map-based guide to help locate ablation gaps using a peak-to-peak voltage (Vpp) map metric.

FIG. 13 is a user interface component that includes a color map based guide to help locate ablation gaps using a $V_{PP}$ map metric. Three color maps I, II and III are shown in the top figure. The interfaces are similar to those previously discussed herein in terms of there A-D row layout. Each color map or user interface element has three columns Left (L), Middle (M), and Right (R). Below each user interface I, II, and III (also labelled as 505, 515, and 525, respectively), a three-dimensional view showing a GSM in 3D with a color coded voltage legend on the left.

The arrangement of user interfaces in FIG. 13 are suitable to help a diagnostic catheter user, such as an HD Grid user, locate ablation gaps using $V_{PP}$ map metric (3D GSM representations) shown on guide. The catheter can be maneuvered across and centered on the ablation line (ABL) (I and II) and then moved in the direction of the ablation line to identify gaps (III) in the line. For clarity $V_{PP}$ map colors are not also shown on the model. Lesion markers 530 simply illustrate the intended continuous lesion ablation line that is being checked for gaps using the $V_{PP}$ color shown on the guide interface. In one embodiment, text or other indicia such can be used to alert a user to the possible occurrence of finding an ablation gap (ABG) or the ablation line (ABL).

Figure 14:
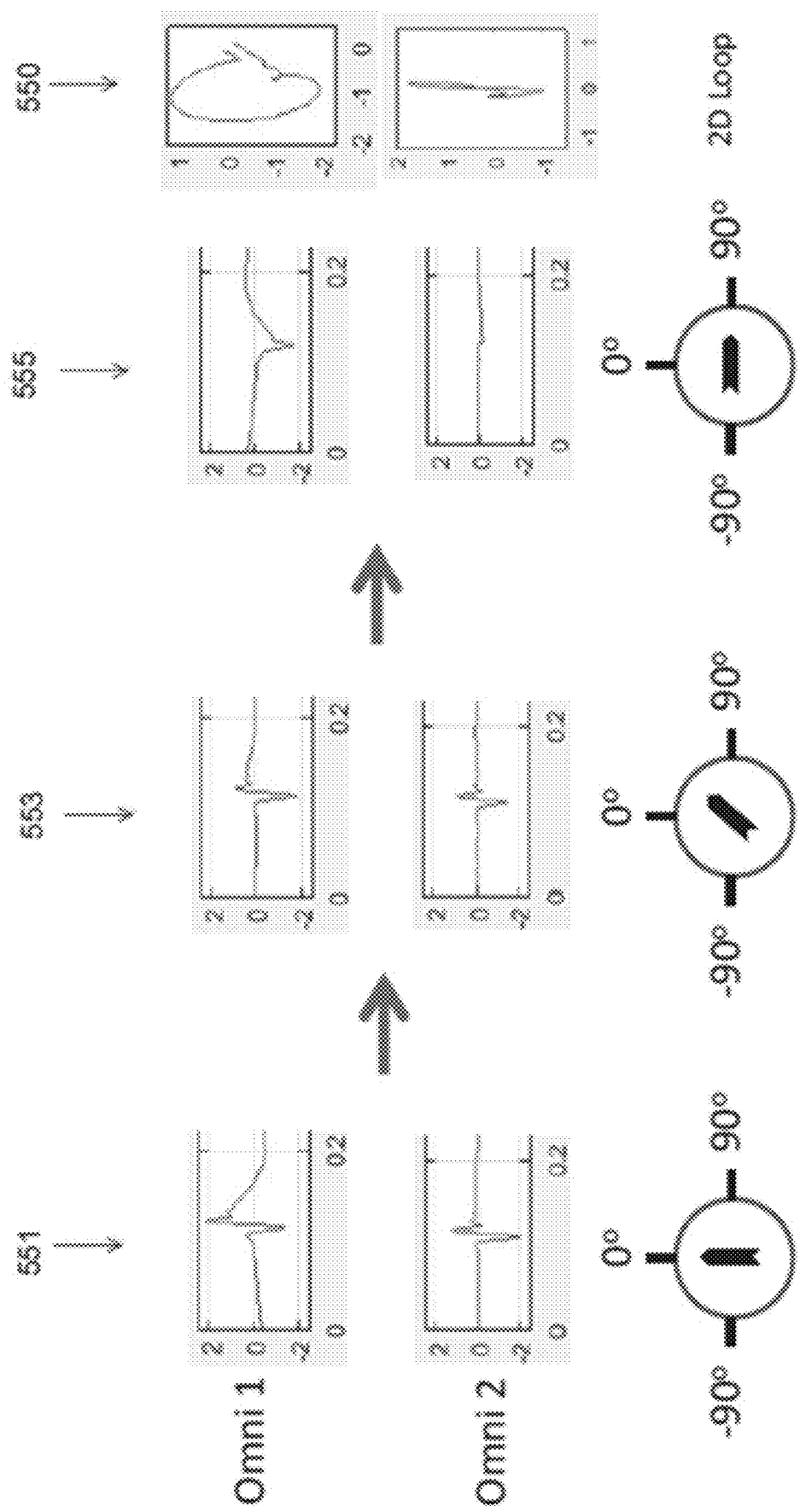
FIG. 14 is a schematic diagram of a user interface that illustrates the effect changes in catheter orientation angle have on omnipolar voltage measurements.

FIG. 14 is a schematic diagram of a user interface that illustrates the effect changes in catheter orientation angle have on voltage measurements. Two rows of omnipolar (omni) traces are shown as Omni 1 and Omni 2. Each row of omni traces is derived from different characteristic 2D loops as shown on the far right side in the column 550. The upper loop corresponding to Omni trace 1 has less eccentricity, while the lower loop is tight and almost linear for Omni trace 2. In addition to the two rows of omnipolar traces and the set of loops 550, the changes to each signal for a given angular measure are shown in columns 551, 553, and 555 with the associated angular measure being displayed in the bottom third row.

Zero degree represents the major axis of the loop and is taken as the m-hat maximal bipole direction. The zero degree orientation is shown in column 551. Moving from left to right, the figure shows omni traces derived from each loop at a 0, 45 (column 553) and 90 degree orientation (column 555). Notice that the orientation change has a greater effect on the Omni 2 signal amplitude compared to the Omni 1 signal amplitude. This results because the Omni 1 loop shape is not very eccentric. 2D loops with high eccentricity are indicative of more homogenous wavefront propagation. In one embodiment, the guide user interface can display eccentricity values for a given E-field loop as a diagnostic parameter.

Figure 15:
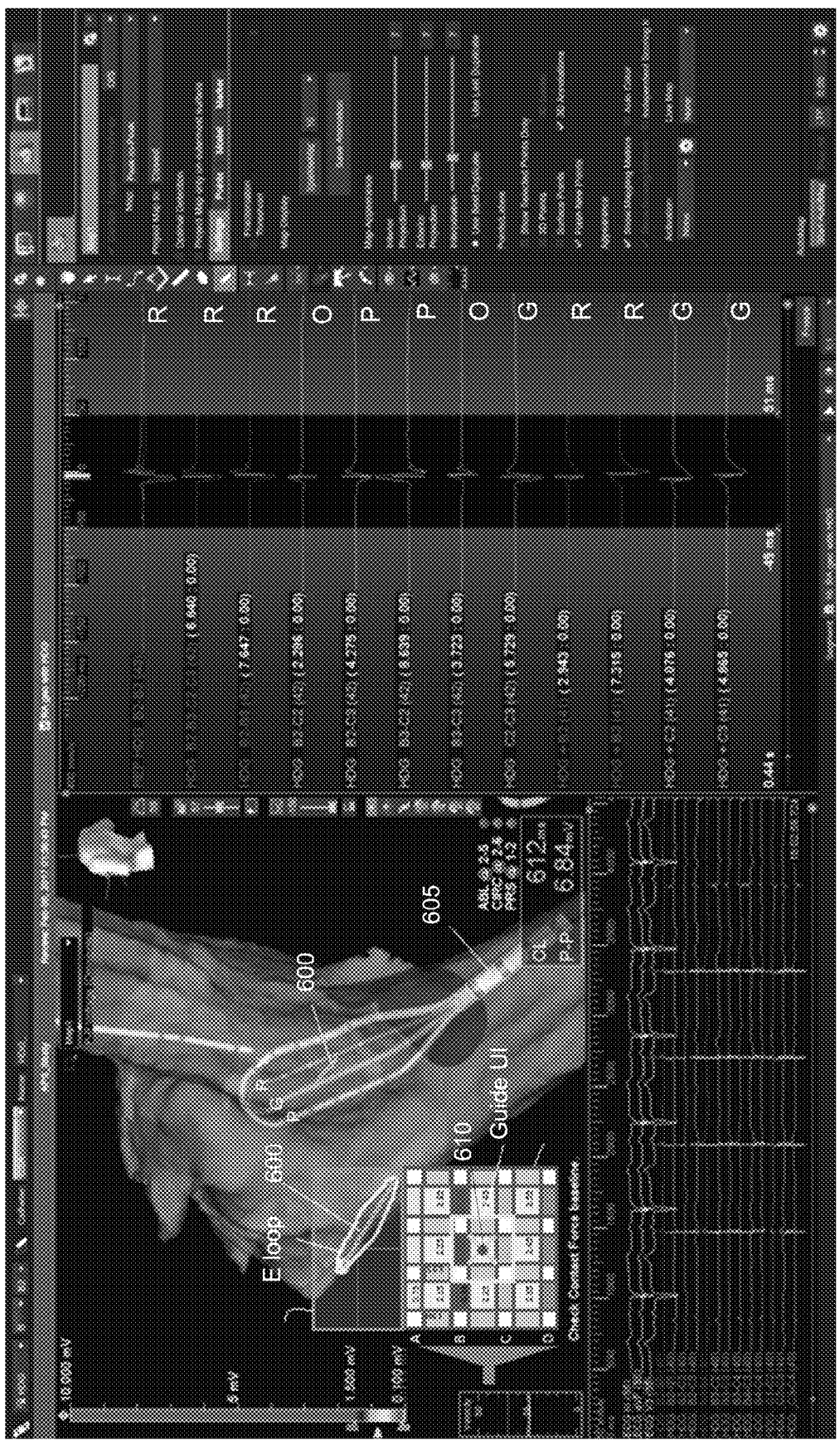
FIG. 15 is user interface display that includes a floating guide interface and an electric field loop interface displayed as an overlay and a m-hat directional element relative to a three-dimensional geometric surface model (GSM) and signal display such as displayed bipoles on a guide interface and a triggered map point acquisition window.

FIG. 15 is a user interface display that includes a floating guide interface and an electric field loop interface displayed as an overlay and a m-hat directional graphic element (green line segment 600). In FIG. 15, the line segment 600 is shown as a line dotted but this is an optional representation. FIG. 15 includes several windows with guide diagram, loop and m-hat within loop display superimposed on the catheter/surface/map display window (top left). The top left user interface window shows a live surface and catheter map display. The bottom left window shows scrolling waveforms of omnipole or bipolar signals. In addition, the right most window shows user interface sliders, toggles, and other controls. The middle column shows the triggered map point acquisition window. Other windows and displays can be zoomed, toggled, or otherwise saved to help with a diagnostic session. The catheter 605 is also represented in the interface and includes color coded splines. Periwinkle (P), green (G), red (R) and yellow (Y) are shown as the associated spline colors but other indicia can be used in lieu of or in addition to color.

In addition with regard to the middle column or panel of the interface and the bottom left panel of the interface, various colors are used as indicium for the various traces shown. Other indicia and labels can be used in various embodiments. As shown in the foregoing middle and bottom panel B2-B3, B3-B4, B2-B3-C2-C3, +B2 and +B3 are identified by the color red (R) or other suitable indicia. Similarly, B2-C2, B3-C3, and B4-C4 are identified by the orange (O) or other suitable indicia. C1-C2, C2-C3, C3-C4, +C2 and +C3 are identified by the color green (G) or other suitable indicia. B2-C1, C2-C3, B3-C2, B3-C4, B4-C3 and B2-C3 are identified by the color periwinkle (P) or other suitable indicia.

In the top left window, a guide user interface (UI) is shown. The guide UI is generally free to be positioned over any part of the display. In one embodiment, as part of the use interface element, catheter splines in the guide interface/diagram are colored to match the same colors and sequence as the catheter in the display window (along splines A-D are colors yellow (Y), red (R), green (G), and blue (B)). The across spline colors are all orange (O) and the diagonal colors are periwinkle (P). Also, the dot 610 in the center clique indicates omnipoles are to be colored red. Other colors and indicia can be used without limitation.

Note the corresponding colors in the map acquisition window (the center window) correspond to the color scheme of the guide interface. In this example, unipolar colors are also shown. Typically, unipole signals would not be selected to appear in an OT voltage map. Although reference to color maps and color is made throughout, in each instance other indicia such as symbols or hatching or other differentiating user interface features can be used. In one embodiment, the guide diagram or guide user interface can be toggled on/off, moved, overlaid and pinned to persist anywhere on the display screen and respond to user actions from one or more input devices.

Figure 16:
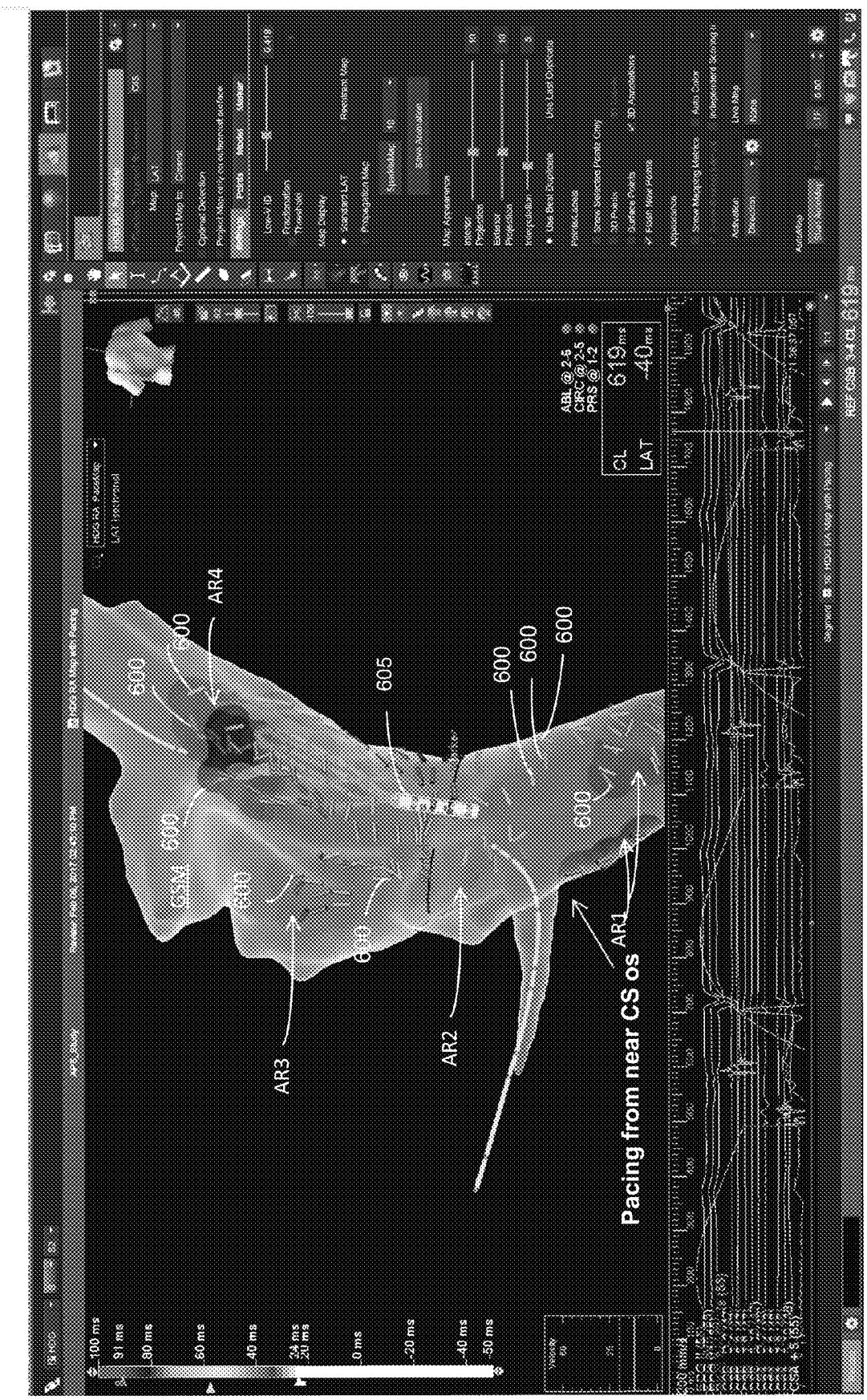
FIG. 16 is a user interface display that shows maximal bipole directions and activation regions using a color map for timing and m-hat directional elements.

FIG. 16 is a user interface display that shows activation directions and activation regions using a color map and m-hat directional elements. M-hat values are shown as line segments 600 and are indicative of an OT voltage mapping. These line segments may be green as shown or indicated using other indicia. The m-hat values generate information in the form of a maximal bipole axis at each OT clique. The line segments 600 obtained provide a sense for activation directions and/or orientations particularly in healthy uniformly conducting tissue. In one embodiment, the m-hat values provide a constrained orientation relative to an axis. In one embodiment, the m-hat values can provide orientation information and can also be combined with other information to provide directional information with regard to activation.

As shown, pacing is from near the coronary sinus ostium. The activation of cardiac tissue tracks the timing legend on the left with green cloud shapes regions being activated first and purple regions being activated last. In this way, activation regions AR1-AR4 evolve in time as multiple regions undergo activation. A color coded legend ranging from −50 ms to 100 ms is shown and can also be coded using hatching or other indicia. The legend starts in the white range, then pink, then red, then orange, then yellow, the green, then blue green, and finally purple. AR1 can be shown using a red color or other indicia. AR2 and AR3 are shown as different colors in the green range of the vertical legend on the left. AR4 is shown as dark blue and transitioning to purple.

The line segments 600 are clustered in each activation region and correspond to maximal bipole axes which are ±180° ambiguous (so no arrow heads are shown). Arrow heads can be shown in various embodiments. Myocardial activation is similarly oriented to OT activation directions in healthy tissue. Pink/Red color shows earliest and purple shows latest activation across the RA, the progression of activation regions AR1 to AR4 tracks this color map. Green bipole axes shown as line segments 600 are well aligned with the activation directions and show the benefit of using m-hat based metrics and the other related metrics described herein.

Exemplary OT Applications, Methods and Further Exemplary Embodiments

Various UI features and display mapping can be used with the OT metrics to enhance diagrams of a catheter such as a high-density grid-based catheter in a static orientation that can be repositioned around the screen. A guide diagram or interface can serve as a floating guide for the purposes of assigning color to certain bipoles (e.g. across and omni) and their associated waveforms. Selecting one or more cliques (triangle or square) for display of their omnipole signals can be performed using the guide interface. Further, the guide interface enables the display of a clique's constituent bipoles so the effect of orientation can be observed on omnipolar signals and peak-peak values. The guide interface also supports showing a color map version of voltage over the catheter. This allows one to readily identify high and low voltage areas and enables selection of the involved cliques for additional scrutiny. It is desirable to investigate the origin of unusual voltages independent of views that may be necessary to maintain or achieve a desired catheter location. A proximity indicator to all catheter electrodes can be shown on the guide interface implemented in the catheter-surface-map display window or in other windows and context.

In one embodiment, maximal bipole direction is ambiguous to ±1800. In one embodiment, it is desirable to choose a direction and force subsequent arrows to be most compatible with that direction. This will address arrow flipping for voltage mapping in some instances. Alternatively consider a single large arrow for the whole of catheter can be displayed should there be substantial agreement in alignment with m-hat (except for the ±180° issue).

Assigning color to certain bipoles (e.g. across and omni) and their associated waveforms can be implemented. This creates matching colors in the guide diagram and the map acquisition window. By this, users can readily distinguish among bipoles and omnipoles and readily understand which waveform type is being viewed.

Selecting one, multiple, or all cliques (triangle or square) for display of their omnipole signals is a feature of the user interface design. Users may decide to focus on small or large numbers of cliques to look into atypical results and interpret them. For example, if the catheter's proximal electrodes are or are not making contact with tissue a user can view the user interface and display features and view fractionated signals, to the extent they are present. This selection makes sense in the geometric context of the guide diagram and other user interface components.

Enabling the display of a clique's constituent bipoles facilitates observing effect of orientation on bipolar signals and their peak-peak values. It also facilitates comparing them to the OT derived signal and its peak-peak value. Confidence in OT and an understanding of directional effects may thus be obtained.

Showing a color map version of voltage over the catheter on the guide interface allows one to readily identify high and low voltage areas and enable selection of the involved cliques is provided in one embodiment. In particular, it is useful to display a colored map of voltage on the guide diagram to provide users with a face-on view of the catheter such that every clique's voltage is clearly depicted. These are not often achieved in the catheter/surface/map display window as views necessary for catheter positioning may not be suited to a face-on view or because of the inclusion-exclusion criteria such as proximity to a cardiac surface suppress visualization of voltage.

In one embodiment, to visualize the degree to which orientation affects voltage, a user control such as a rotatable knob with markings every 90 degrees can be integrated with system 160 or as part of its UI. At 0 degrees, the maximal bipoles are all shown as computed from their individual m-hat maximal bipole directions. As the knob is rotated toward 90 degrees, the bipole amplitudes will decrease (some more than others) and signal shapes change. At 90 degrees (m-hat_perp), the signals will be near minimal and the degree to which their amplitudes are reduced is an index of loop eccentricity and how close propagation resembled a traveling wave. This is believed to help some users understand directional effects as well and how OT employs projection along specific (maximal) directions.

Atrial Voltage Substrate in Atrial Flutter (or Macro Reentrant Organized AF)

The methods and systems can be used in the case of an AF ablation redo with the arrhythmia characterized by an atypical atrial flutter. This may be a macro reentrant arrhythmia in which case an ablation line across the reentrant circuit will terminate the arrhythmia. The catheter allows a user to become certain of the reentrant circuit using a single mapping catheter, combining catheter orientation independent voltage with maximal bipole direction assessments.

By sweeping catheter around in real-time, the clinician observes a narrow tract of conduction with high voltage, consistent directions, bordered by low voltage scar. In concert with the anatomy and conventions for such ablations, a line of block is planned. The narrow tract or isthmus is confirmed by checking that the low voltage borders are not due to catheter orientation effects or lack of contact. Involvement of the isthmus is established by the relatively high voltage, pattern of maximal bipole directions, and perhaps entrainment pacing from a catheter bipole (with a post pacing interval essentially equal to the flutter cycle length). The clinical value is derived from swift identification of the isthmus (which may itself be an ablation line gap) made sure by orientation independent assessments of voltage with inspection of questionable areas.

Vector Field and Spatial Coherence Related Features

Figure 17:
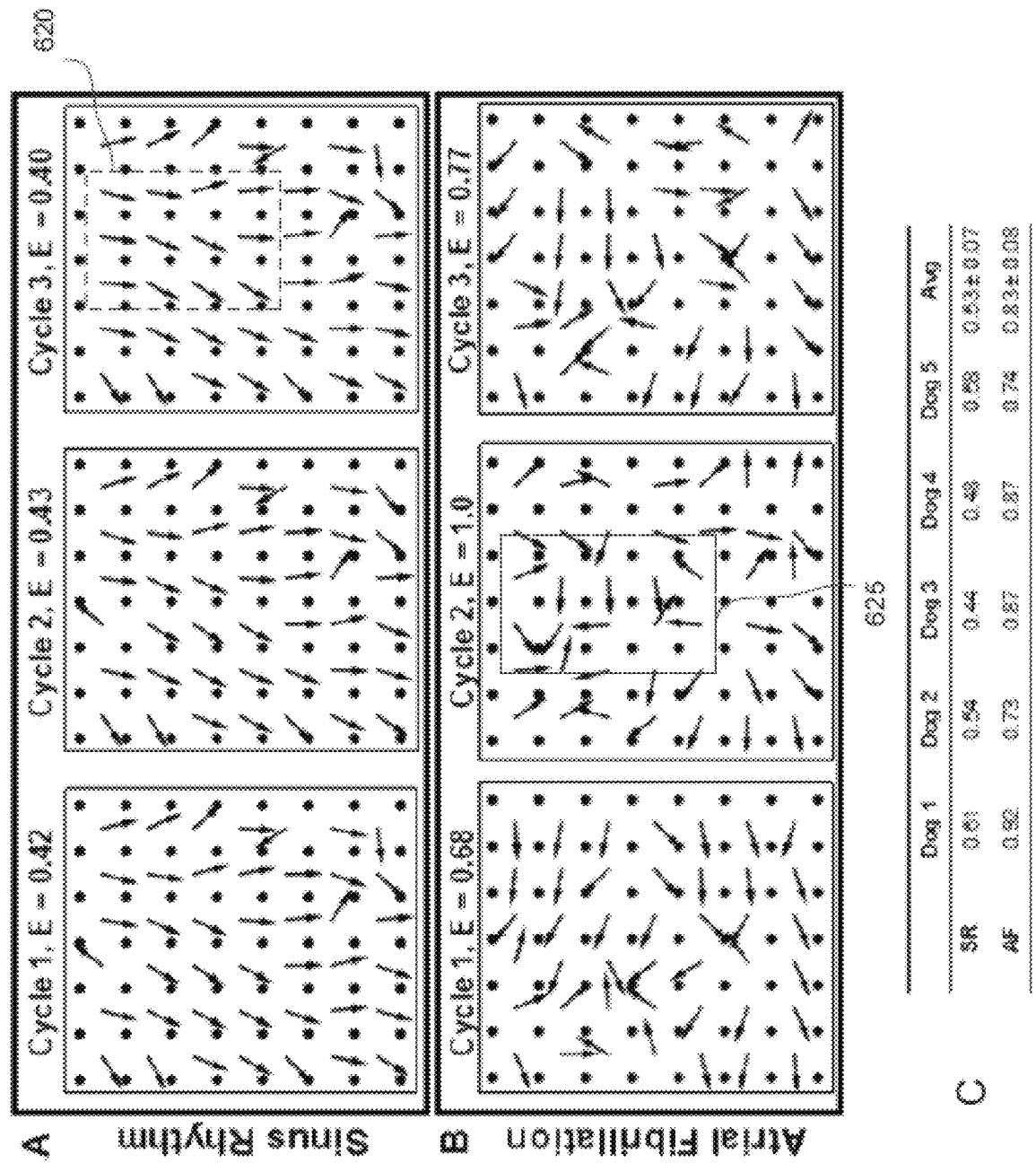
FIG. 17 is data representation diagram that includes two panels (A and B) of vector fields for sinus rhythm (SR) and atrial fibrillation (AF) respectively, and a third panel that includes entropy values over ten heart cycles during SR and AF cycles.

FIG. 17 is data representation diagram that includes two panels (A and B) of vector fields relative to a grid electrode representation generated using sinus rhythm (SR) and atrial fibrillation (AF) measurements, respectively. The third panel (C) of FIG. 17 includes entropy values determined with regard to vector groupings of the respective vector fields over ten heart cycles during SR and AF cycles. In general, the data represented in FIG. 17 can be generated using OT parameters such as m-hat and the other m-hat derived parameters described herein. By comparing different cycles for both SR and AF, along with vector field, vector orientation and derived information, the data representation of FIG. 17 illustrates various diagnostic features such as assessing spatial coherence during AF and SR. Typically, the vector fields are generated using OT parameters described herein such as m-hat. As a result, they are referred to as OT vector fields. Other vector field representations not limited to m-hat or other related parameters can also be used in some embodiments.

As shown in FIG. 17, the representation of the vector fields and their constituent vectors effectively parameterize spatial and temporal organization of vector fields during sinus rhythm and atrial fibrillation by determining their spatial entropies. As the vector field appears more chaotic and jumbled with varying vector orientations, entropy is increasing and spatial coherence is decreasing.

For each beat (in SR) or each cycle (in AF), an OT-vector field is generated within the mapping field being explored using a diagnostic catheter. The spatial Entropy (E) of each OT-vector field is determined using the circular concentration parameter kappa or a scoring or ranking process such as the use of a histogram of the vector angles. During SR, in cycle 3, as shown by region 620, the vectors of the OT-vector field are trending in a shared direction and have similar angular deviations. This region 620 shows low entropy and high coherence. Conversely, during AF, in cycle 2, for example, region 625 shows a cluster of vectors exhibiting high entropy and low coherence.

For a given vector, its orientation relative to a reference line (for example a 2D horizontal line) is recorded. For vectors collinear with the reference line, the vector is assigned a 0° value. In areas where there is coherence or low entropy, clusters of vectors have the same or similar angular measures.

A uniform distribution of angles within the histogram indicates a highly disorganized OT-vector field corresponding to high spatial entropy values. Conversely, if the histogram reflects a narrow range of angles, organization within the OT-vector field is indicated which corresponds to low spatial entropy. Spatial entropy may be determined by $$E = -\sum_{i=1}^{n} P(x_i) \log_b P(x_i)$$

where $P(x_i)$ is a probability density function obtained from the number of vectors in a specific angle bin i and n is the maximum number of angle bins within the histogram. A log base 10 was used for this calculation. The average and standard deviation of entropy values are determined throughout 10 cycles or beats to obtain temporal entropy from the collection of spatial entropies. In panel C of FIG. 17, for the various canines used in the study (Dog 1-Dog 5), entropy values during SR and AF over 10 cycles are depicted for SR and AF. The average entropy values are also shown.

In one embodiment, the organization of wave propagation can also be inferred from the vector fields shown. From FIG. 17, it is clear that SR, with its characteristic spatial and temporal organization of wave propagation, can be affirmed by the low vector field entropy values. During AF however, spatial and temporal disorganization of the vector fields for these three consecutive cycles becomes evident.

Figure 18:
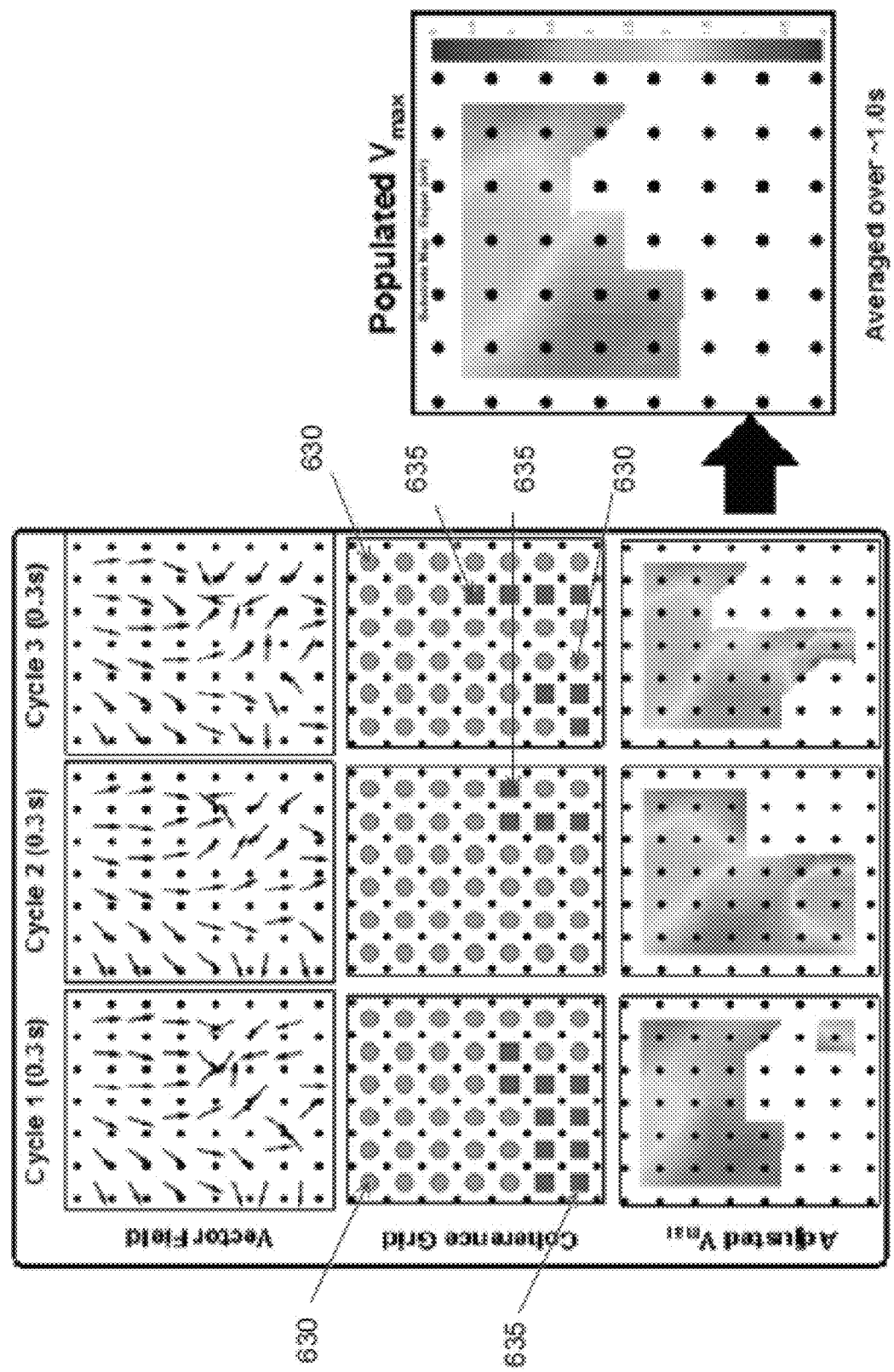
FIG. 18 is data representation diagram for three AF cycles that shows a vector field representation, a coherence grid derived from vector orientation, an adjusted indicia coded Vmax representation and a representation of populated Vmax values selected based on coherent vectors.

FIG. 18 is a data representation diagram for three AF cycles that shows a vector field representation, a coherence grid derived from vector orientation, an indicia coded Vmax representation and an indicia coded representation of populated Vmax values selected based on coherent vectors. The data representation of FIG. 18 illustrates an approach to populate a mapping array using m-hat derived data during AF. In one embodiment, this can be achieved by mapping a catheter electrode representation on an electro-anatomic map.

FIG. 18 illustrates the use of OT vector field coherence-based voltage mapping during SR or AF. For each beat (in SR) or each cycle (in AF), an OT-vector field is generated within the mapping field. A sub-field of the OT-vector field, a 2-by-2 grid that contains four OT unit vectors (e.g. speed is not taken into consideration; only direction is used) is selected for analysis. Within this sub-field, the average length of the four OT unit vectors is determined and used as a spatial coherence score.

If the score is close to 1, then that particular group of OT vectors is spatially coherent. However, if the score is close to 0 that group of OT vectors are spatially incoherent. The score of the four unit vectors is assigned to the spatial location of each of the original vectors within the 2-by-2 subfields. Spatial coherence evaluation is performed repeatedly for all 2-by-2 subfields. In one embodiment, the evaluation is performed with subfields that overlap previously evaluated subfields but include unevaluated vectors or different groupings of previously evaluated vectors.

For instances of vector overlap in subfields, the newly calculated scores are added to the previously calculated scores. With all of the scores calculated and placed at their corresponding spatial location, they are scaled based on the number of overlaps occurring within an area. Further, as part of this scaling, the central area with the greatest number of overlaps has the highest scaling coefficients and the corners with the least number of overlaps having the lowest scaling coefficients. If the final coherence score is larger than 0.5, an area is marked with a green circle (see exemplary regions 630) or another indicia. Otherwise the area is marked with a red circle (or other indicia) (see exemplary regions 635).

These markers (630, 635) assist in determining which parts of the previously created OT voltage maps are to be used to populate a resultant AF voltage map. Low coherence regions 635 are filtered out or not selected. In contrast, coherent areas 630, are not filtered out or otherwise selected. The process is repeated for three or more cycles. Only those Vmax values that are consistently associated with spatially coherent vectors for all three cycles are used to populate a Vmax voltage map. This is but one selection criteria. Other selection criteria can be used. The adjusted Vmax row of FIG. 18 retains Vmax data for the coherent vector regions 630 and removes the Vmax data for the non-coherent vector regions 635. The populated Vmax values shown on the right of FIG. 18 includes the Vmax values that are filtered based on spatial coherence and by temporal consistency over the three cycles. These values range from about 0 to about 5, with the color coded legend progressing from red, to yellow, to green, to light blue, and on to dark blue.

In light of the forgoing, the use of vector fields generated using omnipoles and m-hat based approaches offers various diagnostic tools. By using the calculated vector field for each beat (or cycle), the coherence of neighboring vector clusters can be quantified and evaluated for coherence. In turn, with the spatial coherence map it is possible selectively filter voltage maps to only show electrically viable portions or Vmax areas of interest for further investigation. Further, a comparative evaluation or sum of the results of the coherence selection over multiple cycles can be used to further refine the Vmax target regions for consideration.

Scar Border Mapping and Ablation

Mapping scar borders in subjects with VT episodes is commonly done in sinus rhythm because VT is often not well tolerated. It is also done because reentrant ischemic VT exit sites are commonly found along scar borders and are good ablation targets. Working with a catheter, a region of low voltage may be encountered. The catheter is moved to straddle the high-low voltage transition as OT prevents confounding voltage with electrode orientation. The pattern of voltage may be observed to be high along splines A and B and low along splines C and D. This will often be best seen in the guide diagram as not all cliques produce surface map points and the view angle in the catheter/surface/map display may be poor.

Suspicious of poor contact along the C and D spline side, the clinician rotates the distal catheter trying to bring C and D into better contact. If uniformly high voltage is then observed across catheter, this area is not marked as scar border, reducing the likelihood of ablating healthy myocardium here. Conversely, if voltages remain low and small fractionated potentials are seen supporting tissue contact, a scar border has been defined. Confidence in voltage assessments depends on OT eliminating bipole orientation effects and by facilitating looking at the constituent bipoles. Reliable assessments limiting ablation of ventricular pump muscle to locations where it may be involved in the clinical VT.

Ablation Gap Detection

Checking for gaps in ablation lines may not be as simple as putting a catheter in the pulmonary veins (PVs) and pacing from inside or outside. FIG. 13 shows one implementation of this use case. The catheter and OT voltage mapping helps the clinician locate the ablation lines by noting a sharp transition of voltage and/or timing in their vicinity. With the live voltage display, the clinician moves the catheter along the line and quickly locates a potential low voltage gap.

Cliques at this gap are selected and reviewed to confirm that although some orientation independent bipoles show low voltage, others just 2 mm away show high voltage. This confirms identification of an ablation line gap and serves as a good ablation target. The location may be marked, the catheter withdrawn, and an ablation catheter positioned at the site using a 3D mapping system. By alternating ablation and diagnostic mapping catheters, the patient is subjected to a single cutaneous vascular access site. The diagnostic catheter locates this gap more quickly and with greater certainty than traditional methods.

The disclosure relates to various methods, systems, and apparatus relating to electrical signal generation and detection in the form of electrograms, ECG signals, pacing signals, EP signals and other signals and resultant detected signals and data that are collected or input with regard to a subject. In part, the disclosure includes embodiments and features relating to orientation independent sensing such as described in SYSTEMS AND METHODS FOR ORIENTATION INDEPENDENT SENSING filed on Nov. 17, 2016 and having U.S. Patent Application Pub. No. 20160331471 the entire disclosure of which is incorporated herein by reference.

The use of arrow heads showing directionality in a given figure or the lack thereof are not intended to limit or require a direction in which information can flow. For a given connector, such as the arrows and lines shown connecting the elements shown in FIG. 1A, for example, information can flow in one or more directions or in only one direction as suitable for a given embodiment, whether or not a connector includes an arrow head or is a bi-directional arrow. The connections can include various suitable data transmitting connections such as optical, wire, power, wireless, or electrical connections.

In general, although the use of color and various indicia are referenced and used throughout the application and figures, in each instance a given color or indicia can be replaced with any suitable visual representation or machine readable pattern. Accordingly, for example, colored lines, plots, user interface features, or other graphic elements or indicia described herein or depicted in the figures can be replaced or with hatching, dotted lines, different colors or different indicia or graphic elements without limitation.

Non-Limiting Software Features and Implementations for Disclosed OIS/OT Embodiments The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, computers, multiprocessor systems, microprocessor-based or programmable electronic devices, network PCs, minicomputers, mainframe computers, and the like.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "calculating" or "comparing" or "pacing" or "detecting" or "tracing" or "sampling" "or "thresholding" or "operating" or "generating" or "determining" or "displaying" or "finding" or "extracting" or "filtering" or "excluding" or "interpolating" or "optimizing" or the like, refer to the action and processes of a computer system, or similar electronic data processing apparatus, that manipulates and transforms data represented as physical (electronic) quantities within the computer system's registers and memories into other data similarly represented as physical quantities within the computer system memories or registers or other such information storage, transmission or display devices.

The present disclosure, in some embodiments, also relates to the apparatus for performing the operations herein. This apparatus may be specially constructed for the required purposes, or it may comprise a general-purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the disclosure may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies.

The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing performing feature extraction and processing instructions, or various types of data such as EP data, voltage differences, a relative extremum of differential magnitudes/values, reference triggers, visual and user interface outputs, and other information of interest as described herein. Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value. As used herein, the term "substantially" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

It should be appreciated that various aspects of the claimed disclosure are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the disclosure claimed. Accordingly, what is desired to be secured by Letters Patent is the disclosure as defined and differentiated in the following claims, including all equivalents.

What is claimed is:

1. A method of reducing one or more error types in cardiac system data obtained from a subject using a plurality of electrodes, the method comprising:
defining an error reducing vector $\hat{m}$ by normalizing a differential electric field vector using a magnitude, wherein the differential electric field vector is a difference of a first electric field vector $E(t_j)$ and a second electric field vector $E(t_i)$, wherein $t_i$ and $t_j$ are electric field measurements in time, wherein $t_j > t_i$ and wherein the magnitude is $|E(t_j) - E(t_i)|$;
determining a cardiac system parameter by performing a vector operation comprising
operating, using an operator, upon
(i) $\hat{m}$ or a vector perpendicular thereto $\hat{m}_\perp$ and
(ii) a diagnostic vector, wherein the diagnostic vector is generated using measured cardiac electrogram signals
to generate an output,
wherein the output is a scalar output or a vector output; and
displaying the output or information correlated with the output.

2. The method of claim 1 further comprising maximizing $|E(t_j) - E(t_i)|$.

3. The method of claim 1 wherein the operator is a dot product operator, wherein the diagnostic vector is $E(t)$, and wherein the output of $<\hat{m}, E(t)>$ is a scalar electrical field signal $E_m(t)$.

4. The method of claim 3 further comprising computing a peak to peak value of $E_m(t)$.

5. The method of claim 3 further comprising determining a scalar voltage signal $V_m(t)$, wherein $V_m(t)$ comprises a product of k and $E_m(t)$, wherein k is an electrode spacing between the plurality of electrodes.

6. The method of claim 5 further comprising computing a peak to peak value of $V_m(t)$.

7. The method of claim 1 wherein the operator is a dot product operator, wherein the diagnostic vector is E(t), and wherein the output of $<\hat{m}\bot, E(t)>$ is a scalar electrical field signal $E_{m\bot}(t)$.

8. The method of claim 1 further comprising determining one or more directional deviations between $\hat{m}$ and $\hat{a}$ and generating an alert when the one or more directional deviations exceeds a threshold, wherein the direction of $\hat{a}$ is an activation direction.

9. The method of claim 8 wherein the threshold is an angular deviation between that ranges from about 15 degrees to about 20 degrees.

10. The method of claim 1 wherein the one or more error types comprises directionality-based errors and further comprising reducing directionality-based errors.

11. The method of claim 1 further comprising displaying one or more graphic user interface elements aligned with $\hat{m}$ relative to a 2D or 3D display of a cardiac tissue representation.

12. The method of claim 1 further comprising displaying the one or more graphic user interface elements corresponding to or aligned with $\hat{m}$ relative to one or more regions of detected cardiac tissue activation.

13. The method of claim 1 further comprising displaying a graphic user interface element that comprises a plurality of user selectable elements, wherein the user selectable elements comprise a plurality of triangular electrode cliques and a plurality of square electrode cliques.

14. The method of claim 13 wherein, in response to user selection of one or more of the square electrode cliques or triangular electrode cliques, one or more waveforms associated with each clique selected is displayed.

15. The method of claim 13 wherein the graphic user interface element is a guide diagram comprising a representation of an array of electrodes for a diagnostic catheter and one or more indicia, wherein the indicia corresponds to a parameter selected from the group consisting of a bipole voltage, a unipole voltage, a unipole wave form, a bipole waveform, an ablation gap, and an activation direction.

16. The method of claim 15 wherein the indicia is a color and further comprising displaying a color coded legend comprising the color.

17. The method of claim 1 further comprising measuring a plurality of electrical signals from cardiac tissue during atrial fibrillation and characterizing spatial coherence of a vector field derived using the cardiac system parameter.

18. The method of claim 17 wherein the step of characterizing is performed using a coherence or entropy measurement of one or more vectors of the vector field.

19. The method of claim 17 wherein the step of characterizing is performed by coherence filtering Vmax values on a per cycle basis and comparing filtered results for each cycle to exclude inconsistent regions between different cycles.

20. A method of generating a reference signal suitable for comparison to one or more cardiac tissue measured signals, the method comprising
selecting a clique of connected unipoles in a non-linear arrangement;
converting combination of selected unipoles and associated bipoles to electric field components;
converting electric field components to electrical potential signals $V_x$ and $V_y$, wherein x and y are axes of catheter reference frame; and
normalizing $V_x$ and $V_y$ signals to generate a direction independent signal, wherein normalizing $V_x$ and $V_y$ signals comprises determining a Euclidean magnitude.

21. The method of claim 20 further comprising:
filtering the direction independent signal to generate a filtered direction independent signal, wherein the filtered signal is directionally independent.

22. The method of claim 21 wherein the step of filtering comprises one or more steps selected from the group consisting of reducing an error associated with detection of depolarizations, low pass filtering, differentiating, and signal thresholding.

23. The method of claim 21 further comprising processing the filtered direction independent signal using a refractory period of cardiac tissue, a noise floor, and a zero-crossing detector to detect polarization events in the filtered signal.

24. The method of claim 20 wherein the step of converting the combination of selected unipoles and associated bipoles is performed by performing a least squares fit.

* * * * *